US010713458B2

(12) United States Patent
Bhat et al.

(10) Patent No.: US 10,713,458 B2
(45) Date of Patent: Jul. 14, 2020

(54) INTEGRATED LIGHT EMITTING DISPLAY AND SENSORS FOR DETECTING BIOLOGIC CHARACTERISTICS

(71) Applicant: InSyte Systems, Newark, CA (US)

(72) Inventors: Jerome Chandra Bhat, Palo Alto, CA (US); Richard Ian Olsen, Truckee, CA (US)

(73) Assignee: InSyte Systems, Newark, CA (US)

(*) Notice: Subject to any disclaimer, the term of this patent is extended or adjusted under 35 U.S.C. 154(b) by 172 days.

(21) Appl. No.: 15/618,043

(22) Filed: Jun. 8, 2017

(65) Prior Publication Data
US 2017/0337413 A1 Nov. 23, 2017

Related U.S. Application Data

(63) Continuation-in-part of application No. 15/600,480, filed on May 19, 2017.
(Continued)

(51) Int. Cl.
G06K 9/00 (2006.01)
F21V 8/00 (2006.01)

(52) U.S. Cl.
CPC ......... G06K 9/0002 (2013.01); G02B 6/0035 (2013.01); G02B 6/0036 (2013.01);
(Continued)

(58) Field of Classification Search
CPC .... G06K 2009/00932–00939; G06K 9/00892; G06K 9/00006; G06K 9/00013;
(Continued)

(56) References Cited

U.S. PATENT DOCUMENTS 7,177,451 B2 * 2/2007 Higuchi ............... G06K 9/0004
382/124
7,876,929 B2 * 1/2011 Matsumura .......... A61B 5/1172
382/115
(Continued)

FOREIGN PATENT DOCUMENTS

EP 2131322 A1 12/2009
EP 2983109 A2 2/2016
(Continued)

OTHER PUBLICATIONS

PCT/US2017/036881 filed Jun. 9, 2017, "International Search Report and Written Opinion" 10 pages.
(Continued)

Primary Examiner — Michael S Osinski
(74) Attorney, Agent, or Firm — Patent Law Group; Brian D. Ogonowsky

(57) ABSTRACT

A bio-sensor device, integrated with a display portion, includes a surface for touching by a body part, such as a finger. A light source, such as an array of LEDs, emit light through the surface so as to be reflected and partially absorbed by the body part An array of photodetectors detects light reflected back by the body part and generates signals corresponding to an image of the light reflection, which corresponds to the light absorption pattern in the body part. The light absorption pattern may correlate to a fingerprint, a blood vessel pattern, blood movement within the blood vessels, combinations thereof, or other biometric feature. A processor receives the signals from the photodetectors and analyzes the signals to determine a characteristic of the body part. The characteristic may be used to authenticate the user of the bio-sensor device by comparing the detected characteristic to a stored characteristic.

20 Claims, 9 Drawing Sheets

Related U.S. Application Data

(60) Provisional application No. 62/348,096, filed on Jun. 9, 2016, provisional application No. 62/340,218, filed on May 23, 2016.

(52) U.S. Cl.
CPC ......... *G06K 9/0004* (2013.01); *G06K 9/0012* (2013.01); *G06K 9/00067* (2013.01); *G06K 9/00087* (2013.01); *G06K 9/00496* (2013.01); *G02B 6/0093* (2013.01)

(58) Field of Classification Search
CPC .... G06K 9/0002–0008; G06K 9/00107–0012; G06K 9/00885; G06K 9/2018; G06K 9/00067; G06K 9/00496; A61B 5/1172; A61B 5/489; A61B 5/117; A61B 5/6826; A61B 5/0261; G06F 3/044; G06F 21/32; G06F 21/83; G06T 7/0002–0012
See application file for complete search history.

(56) References Cited

U.S. PATENT DOCUMENTS

| | | | |
|---|---|---|---|
| 7,961,918 B2 | 6/2011 | Hikita et al. | |
| 8,787,624 B2 | 7/2014 | Hama et al. | |
| 8,923,573 B2 * | 12/2014 | Shinzaki | G06F 21/32 382/115 |
| 9,020,226 B2 | 4/2015 | Kamei | |
| 9,195,900 B2 | 11/2015 | Gu et al. | |
| 9,466,653 B2 | 10/2016 | de Jong et al. | |
| 9,570,002 B2 | 2/2017 | Sakariya et al. | |
| 10,140,536 B2 | 11/2018 | Hung et al. | |
| 2003/0044051 A1 * | 3/2003 | Fujieda | G06K 9/00067 382/124 |
| 2003/0090650 A1 * | 5/2003 | Fujieda | G06K 9/0004 356/71 |
| 2004/0208346 A1 * | 10/2004 | Baharav | G06F 3/0317 382/124 |
| 2005/0123176 A1 * | 6/2005 | Ishii | G06K 9/00026 382/124 |
| 2005/0237317 A1 * | 10/2005 | Cok | G06F 3/0421 345/207 |
| 2006/0098848 A1 | 5/2006 | Nagasaka et al. | |
| 2006/0115128 A1 | 6/2006 | Mainguet | |
| 2007/0036399 A1 | 2/2007 | Matsumura et al. | |
| 2007/0041005 A1 | 2/2007 | Song et al. | |
| 2007/0253607 A1 * | 11/2007 | Higuchi | G06K 9/00026 382/124 |
| 2008/0008365 A1 | 1/2008 | Hikita et al. | |
| 2008/0232653 A1 | 9/2008 | Rowe | |
| 2008/0317303 A1 | 12/2008 | Konno et al. | |
| 2009/0039241 A1 * | 2/2009 | Ueki | A61B 5/0059 250/227.14 |
| 2009/0074255 A1 * | 3/2009 | Holm | G06K 9/0004 382/115 |
| 2009/0074263 A1 | 3/2009 | Higuchi | |
| 2009/0245591 A1 | 10/2009 | Rowe et al. | |
| 2010/0008545 A1 | 1/2010 | Ueki et al. | |
| 2010/0164906 A1 * | 7/2010 | Fukunaga | G06F 3/0412 345/175 |
| 2010/0283765 A1 * | 11/2010 | Gotoh | G06F 3/0412 345/175 |
| 2011/0007951 A1 | 1/2011 | Mil'shtein et al. | |
| 2011/0187653 A1 | 8/2011 | Ko et al. | |
| 2011/0187679 A1 * | 8/2011 | Ko | G06F 3/042 345/175 |
| 2011/0200237 A1 | 8/2011 | Nakamura et al. | |
| 2013/0129164 A1 | 5/2013 | Gu et al. | |
| 2013/0136327 A1 | 5/2013 | Kamei | |
| 2014/0028575 A1 | 1/2014 | Parivar et al. | |
| 2015/0146944 A1 | 5/2015 | Pi et al. | |
| 2015/0193669 A1 | 7/2015 | Gu et al. | |
| 2015/0346856 A1 * | 12/2015 | Wassvik | G06F 3/042 345/175 |
| 2015/0364107 A1 | 12/2015 | Sakariya et al. | |
| 2016/0042219 A1 | 2/2016 | Bae et al. | |
| 2016/0132712 A1 | 5/2016 | Yang et al. | |
| 2016/0239151 A1 * | 8/2016 | Sun | G06F 3/0421 |
| 2016/0342282 A1 * | 11/2016 | Wassvik | G02F 1/13338 |
| 2017/0076133 A1 * | 3/2017 | Hillmann | G06T 7/11 |
| 2017/0220841 A1 * | 8/2017 | Maeda | G06F 3/041 |
| 2017/0228125 A1 * | 8/2017 | Lee | G06F 3/0421 |
| 2018/0211085 A1 * | 7/2018 | Liu | G02F 1/13306 |
| 2018/0267651 A1 * | 9/2018 | Park | G06F 3/017 |
| 2018/0322325 A1 * | 11/2018 | Lee | G06K 9/0004 |
| 2019/0033976 A1 * | 1/2019 | Cao | G06F 3/017 |

FOREIGN PATENT DOCUMENTS

| | | |
|---|---|---|
| JP | 2008212311 A | 9/2008 |
| JP | 2008308037 A | 12/2008 |
| JP | 2009003821 A | 1/2009 |
| JP | 2010131180 A | 6/2010 |
| JP | 2016038913 A | 3/2016 |

OTHER PUBLICATIONS

PCT/US2017/033859 filed May 22, 2017, "International Search Report and Written Opinion" dated Aug. 14, 2017, 10 pages.

* cited by examiner

INTEGRATED LIGHT EMITTING DISPLAY AND SENSORS FOR DETECTING BIOLOGIC CHARACTERISTICS

CROSS-REFERENCE TO RELATED APPLICATIONS

This application is a continuation-in-part of U.S. application Ser. No. 15/600,480, filed on May 19, 2017, and is based on and claims priority from U.S. provisional patent application Ser. No. 62/348,096, filed on Jun. 9, 2016, by Jerome Chandra Bhat, and U.S. provisional patent application Ser. No. 62/340,218, filed on May 23, 2016, by Jerome Chandra Bhat and Richard Ian Olsen, assigned to the present assignee and incorporated herein by reference.

FIELD OF THE INVENTION

This invention relates to the sensing of biologic characteristics, such as blood flow, blood components, fingerprints, blood vessel patterns, a face, etc. and, in particular, to the sensing of such characteristics using light and photodetectors.

BACKGROUND

It is known that applying light of particular wavelengths (e.g., red or IR) to a human body part (e.g., a finger) and measuring the light transmitted through the body part can be used to detect blood flow (e.g., a pulse), components in the blood (such as hemoglobin), fat, and other characteristics. Generally, the light absorption correlates to particular characteristics.

However, such systems are generally limited to medical devices performing only a single function. Further, since the measurement of light absorption is through the body part, the device must be specifically made to surround the particular body part being tested, such as a finger.

What is needed is a more flexible and compact biologic sensor that can be used for a variety of functions and can be used for medical as well as non-medical purposes, such as authentication of the user. For user authentication, the biologic sensor should be able to be easily integrated into existing consumer products.

U.S. Pat. No. 9,570,002, in column 31, describes adding IR LED emitters into the matrix of a full color display screen along with photodetectors. The user may then touch the screen, and an image of the user's fingerprint may be detected by detecting the reflection off the ridges of the fingertip touching the screen. The detection is only of the surface of the fingertip and does not measure any light absorption at a depth into the finger, such as to detect a blood vessel or blood flow. Therefore, if the device is used for authentication, a simulated/forged fingerprint can fool the device. Additionally, the display screen is an array of closely packed red, green, and blue LEDs, and it is difficult to add IR LEDs and photodetectors into the existing array of LEDs without losing resolution. Further, it would be very expensive to develop a new display screen with integrated display pixels and detection pixels.

SUMMARY

An integrated and compact light emitter and sensor device is described that can be used to detect biologic characteristics of the person using the device. The characteristics can be used for medical/diagnostic purposes as well as authentication of the person. For example, the device may be installed in a smart phone, a computer, or even a gun to authenticate the user.

In one embodiment, high resolution pixels formed by multi-wavelength light sources, such as LEDs or filtered white light, provide light that penetrates a body part, such as a finger, when applied to the skin. An array of photodetectors is integrated in the light emitter and detects the magnitude of light reflected back from the body part, where the magnitude of the light reflected back is affected by absorption of the light by the body part. The array of photodetectors may create a high resolution image of the light absorption. The pixels (e.g., emitted wavelengths) may be controlled to target certain biologic characteristics, and the resolution of the device may be high to detect detailed characteristics, such as fingerprints and blood vessel patterns. A video image may even be captured. Optics may be used to detect the absorption only at a certain depth into the skin, such as for detecting the location of blood vessels. A processor in the device may be programmed to analyze the signals from the photodetectors and generate results, such as authentication of the user.

Since it would be very difficult to forge both a fingerprint and a blood vessel pattern, the device has a much higher reliability for authentication compared to only a fingerprint detector.

In another embodiment, LED light (e.g., IR light) is coupled into an edge of a transparent light guide, and the light is guided within the light guide by TIR due to the very different indices of refraction of the light guide and air. Assuming a user's finger is pressed on the light guide surface, such as glass, for fingerprint detection, the refractive indices of the finger and the glass are closely matched. The fingerprint crests (ridges) contact the glass surface while the troughs will produce an air gap. Accordingly, light will be pulled out from the light guide into the finger only in the pattern of the crests. Therefore, the light guide may be transparent. A high resolution photodetector array is positioned behind the light guide. Light reflected off a body part (e.g., a finger) contacting the top surface of the light guide is then transmitted back through the light guide and detected by the photodetector array. The device may optionally also operate as a display, with the display pixels behind the light guide. The resulting detected image may be used for authenticating the user by a fingerprint, blood vessel pattern, or other combination of biologic characteristics. In one embodiment, the light guide is also the display glass for a display screen laterally spaced from the detector portion, so the detector and display are integrated. The display pixels may be conventional, such as OLEDs, and only the detector light source uses the display glass as a light guide. By using the display glass for the dual purpose of a light guide and a protective layer for the display (or a touch screen for the display), there is synergy and integration, and the TIR uniformly spreads the light for the fingerprint/blood vessel detection. The light source for the detector may be optically coupled near any edge of the display glass.

The detector array may be distributed throughout the display pixels or laterally spaced from the display portion.

Light will enter a distance into the finger via the fingerprint crests and also scatter within the finger and become absorbed by blood vessels within a certain depth. This will create a secondary reflection pattern that can be used in conjunction with the fingerprint pattern to detect the positional relationship between the fingerprint and blood vessel pattern. The fingerprint pattern will be high contrast, while the blood vessel pattern will effectively be superimposed over the fingerprint pattern.

In one embodiment, the light source and light sensor portion are spaced laterally from the display pixels, such as along one side of the display portion, so as not to use up any space in the display portion. The display portion emits light through a light passing panel, such as a thin glass panel, for generating an image. The glass panel may even include a capacitive touch sensor. A light source for the bio-detector portion is laterally spaced from the display portion, such as next to the light sensor portion, or the light source is optically coupled to an edge of the light passing panel and the light passing panel acts as a waveguide for the light source, as previously described. The detection is thus through an area separate from the display area. The light source may emit IR light while the display portion emits red, green, and blue light from an array of pixels. In this way, the light source and detector portion do not affect the display portion, while both the display portion and detector portion use the same light passing panel. Accordingly, the display and sensor are integrated but are laterally spaced.

The device may also be used as a pulse sensor or as sensor for certain blood components that absorb a target wavelength.

Different LEDs emitting different wavelengths may be separately energized, and the reflected light is detected by a broad spectrum photodetector to determine different types of biologic features of the body part.

Optics may be used to focus the light to detect biologic features only at a certain depth into the body part, such as blood vessels.

Additional sensors may be integrated into the optical sensor, such as a gas sensor, electrodes for detecting a pulse, etc.

The devices may be compact and inexpensive, allowing their use in portable devices for authentication or for an analysis of the user's biologic characteristics.

Various other designs and uses of such devices are described.

BRIEF DESCRIPTIONS OF DRAWINGS

Figure 4:
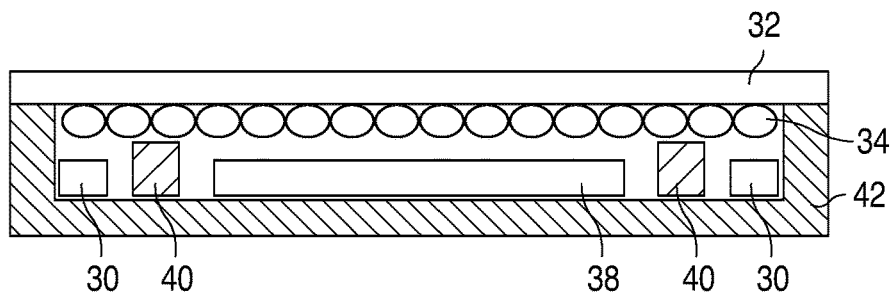

FIG. 4 is a cross-sectional view of another embodiment of a device that includes a light source and photo-sensors for detecting biologic characteristics, where the light is injected into edge portions of a transparent or translucent light guide and emitted from a front surface of the light guide, and where a photo-diode array is positioned behind the light guide for detecting an image of the absorption of light by the person's body part.

Figure 5:
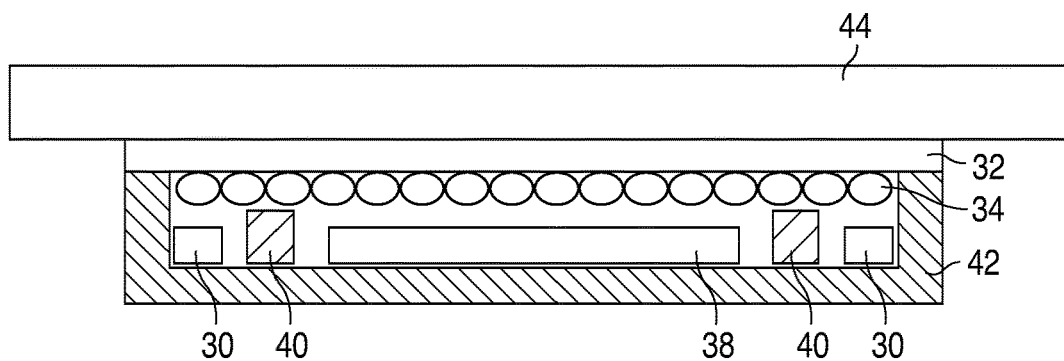

FIG. 5 illustrates the device of FIG. 4 affixed to a transparent layer, such as a protective outer layer of a smart phone, laptop computer, or other consumer device.

Figure 6:
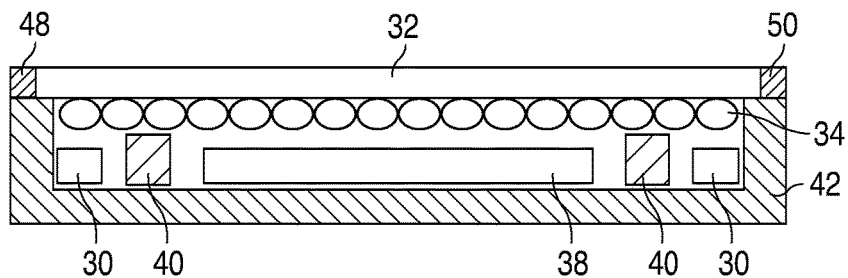

FIG. 6 illustrates the device of FIG. 4 augmented with electrodes for sensing an electrical signal from the person's body part, such as for detection of EKG signals, in combination with detection of the reflected light.

Figure 7:
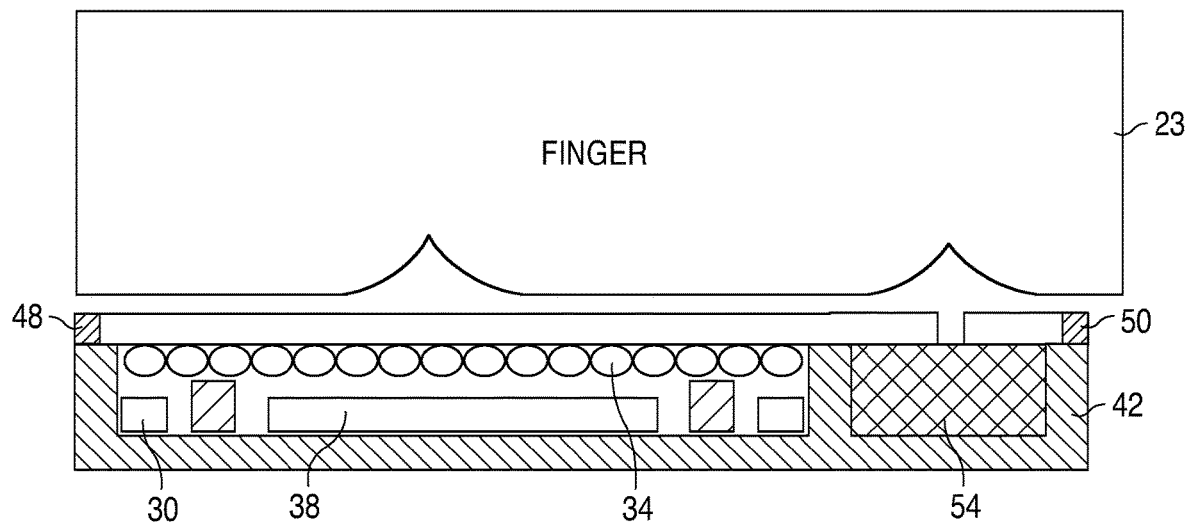

FIG. 7 illustrates the device of FIG. 5 further augmented with a sensitive gas sensing element for detecting gasses emanating from the person.

Figure 8:
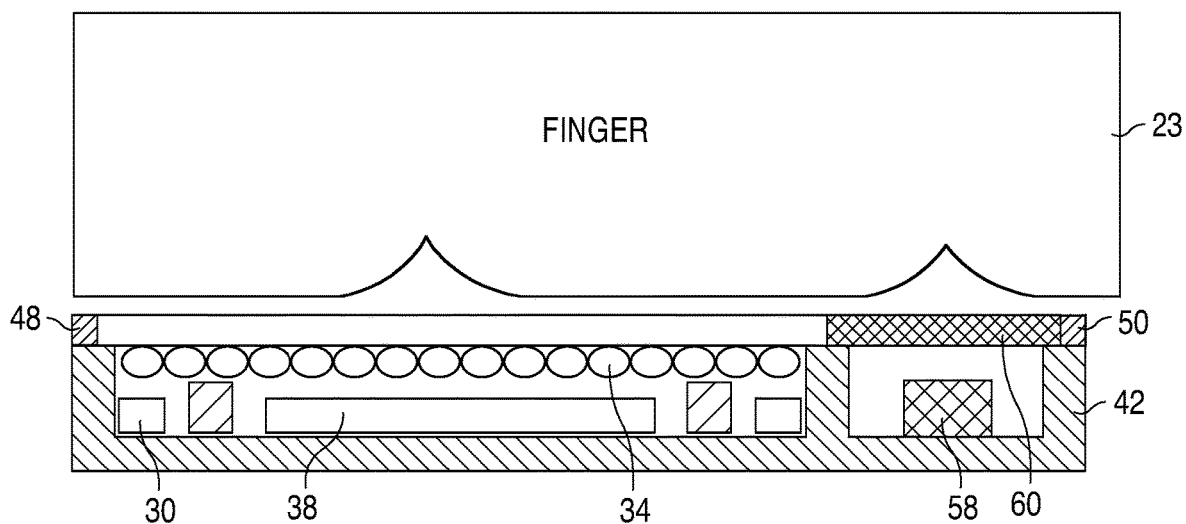

FIG. 8 illustrates the device of FIG. 6 further augmented with a non-contact, infra-red temperature sensor for determining the temperature of the body part (e.g., a finger) in contact with the device.

Figure 9:
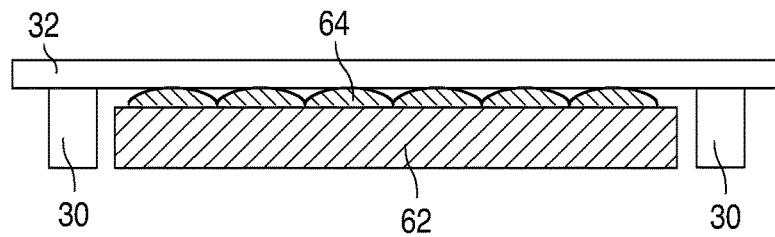

FIG. 9 illustrates another embodiment of the invention where focusing lenses are abutting the photosensor array for higher resolution, for a higher signal-to-noise ratio, and for forming a more compact device.

Figure 10:
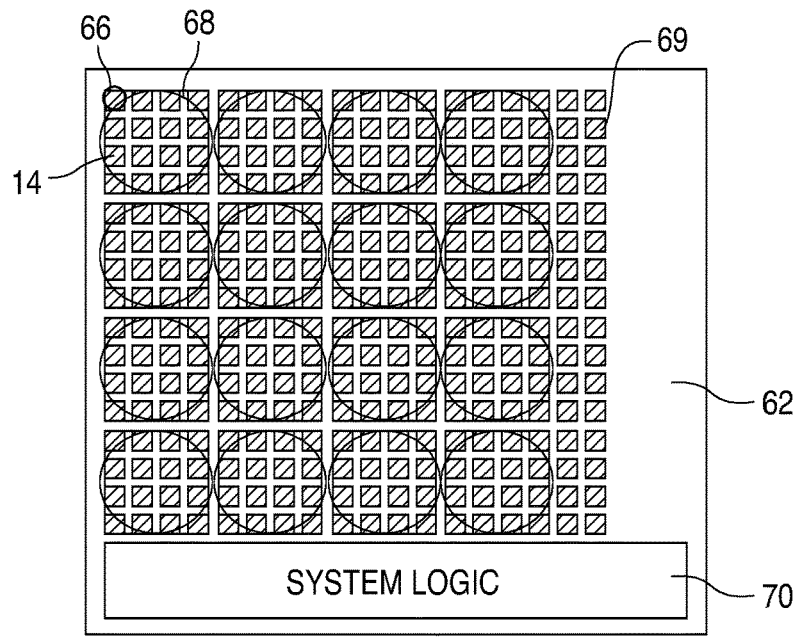

FIG. 10 is a front view of a single integrated circuit chip having a high resolution array of photodetectors. A lens array is positioned over the detector array, which focuses the incoming light and which reduces the amount of direct light entering the photodetectors for increasing the signal-to-noise ratio. A light source may have many suitable designs, such as a transparent light guide that emits light only in the direction of a person's body part in contact with the light guide. Reflected light is transmitted back through the light guide to the photodetectors.

Figure 11:
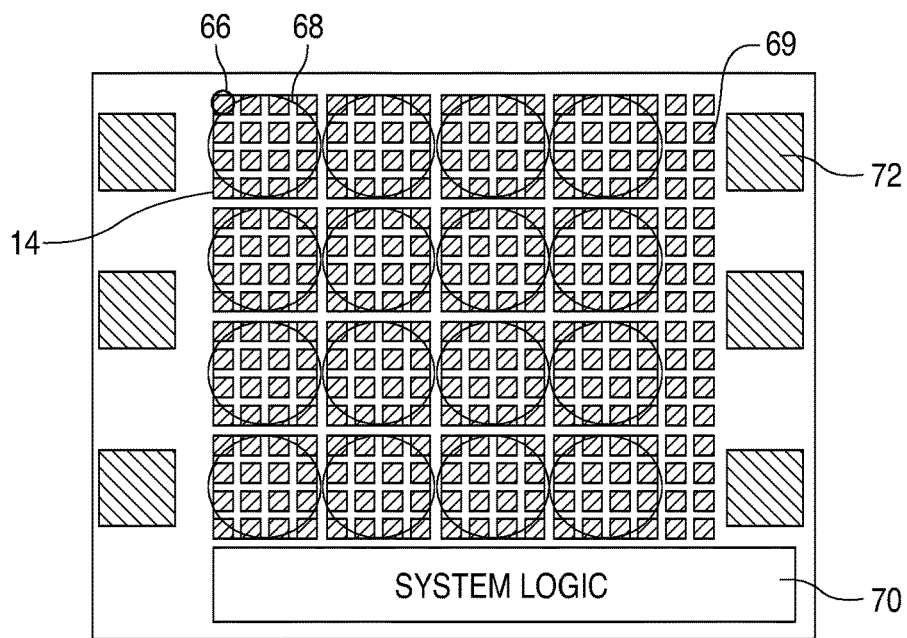

FIG. 11 is similar to FIG. 10 but integrates the light sources (e.g., LEDs or lasers) on the same surface as the photodetectors.

Figure 12:
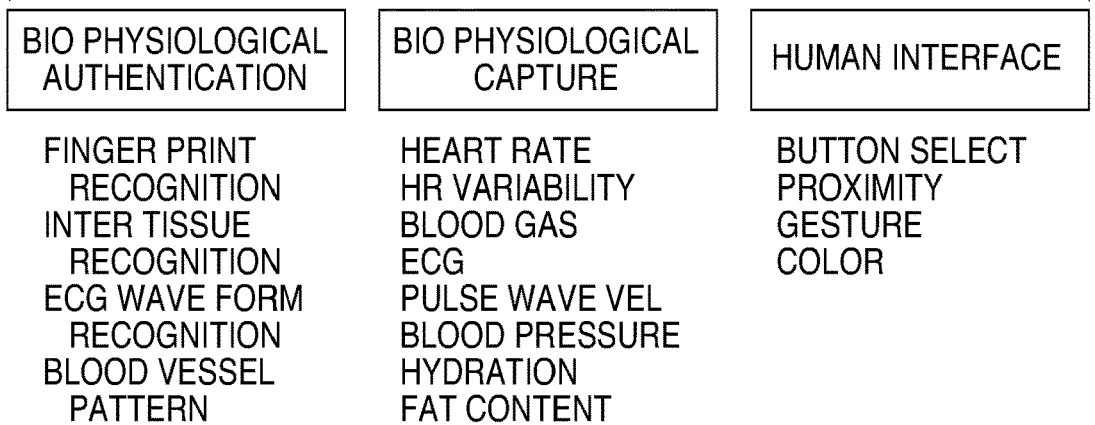

FIG. 12 identifies functions that may be performed with the various devices.

Figure 13:
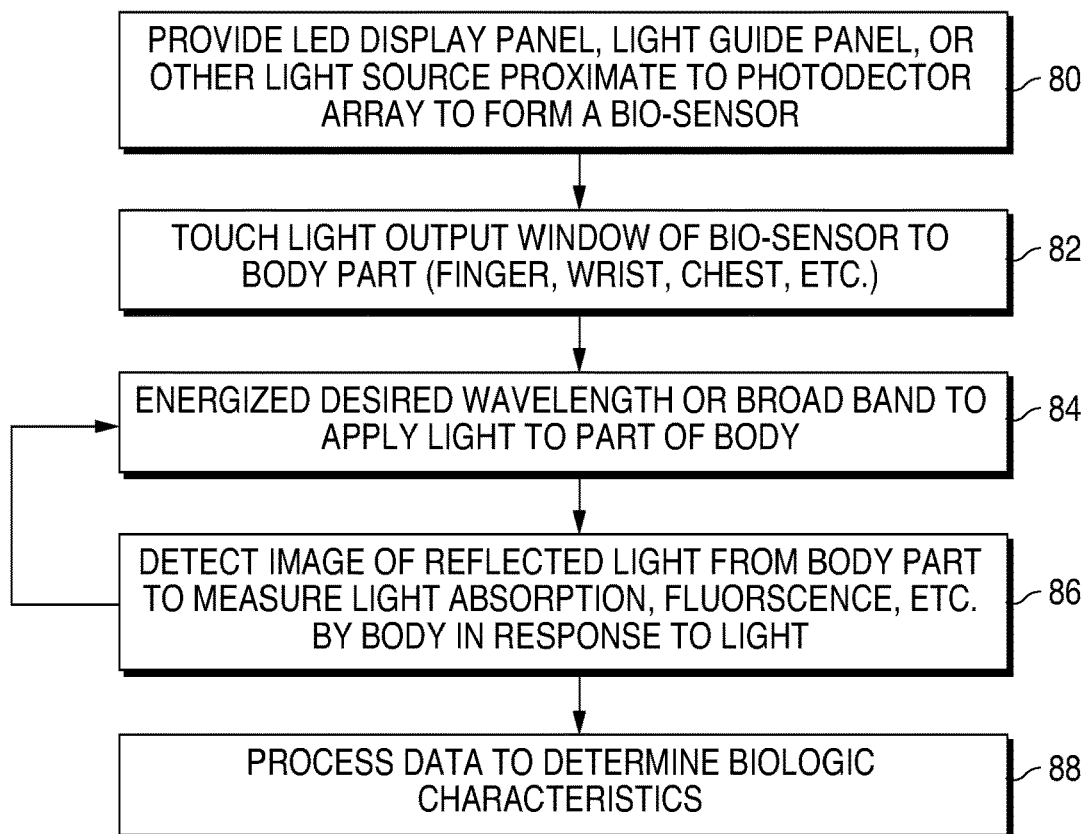

FIG. 13 is a flowchart of an example of basic steps performed by the device to detect biologic characteristics of the user.

Figure 14:
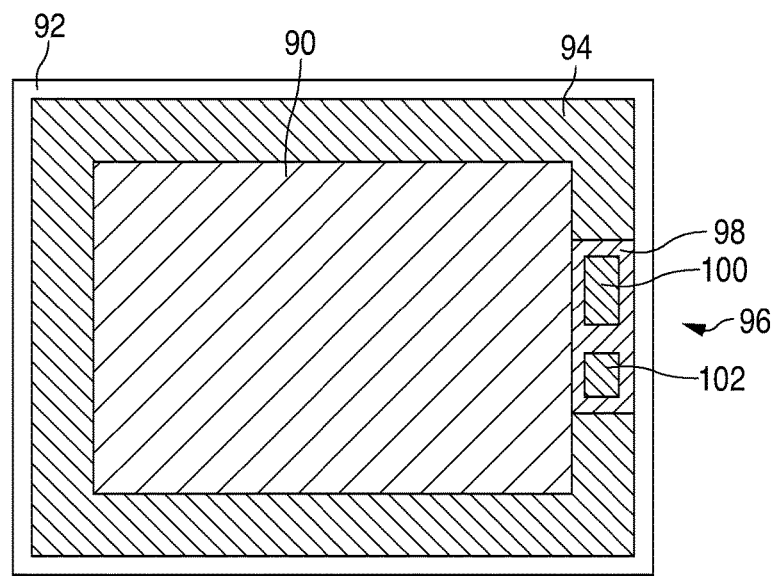

FIG. 14 is a top down view of another embodiment of an integrated sensor and display, where the sensor portion is laterally spaced from the display portion but uses the same cover glass as the display portion.

Figure 15:
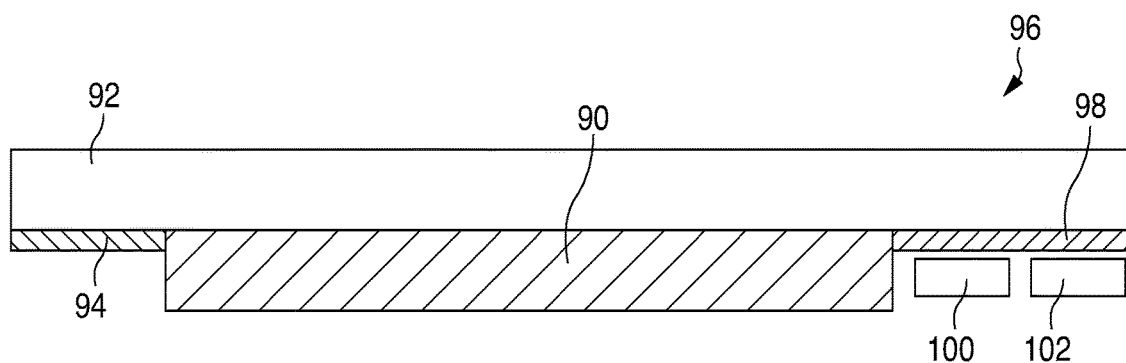

FIG. 15 is a cross-sectional view of the device of FIG. 14 showing the sensor portion and IR emitter laterally spaced from the display portion so as not to affect the display portion. The sensor and IR emitter are shown side-by-side in FIG. 15, in contrast to a more accurate cross-section of FIG. 14, for ease of understanding.

Figure 16:
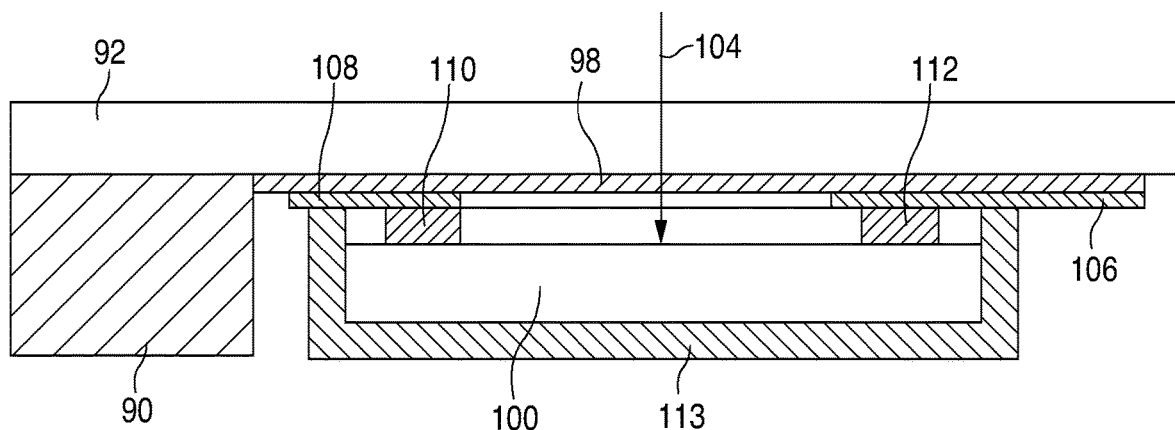

FIG. 16 is a cross-sectional view of an integrated display/sensor showing more detail of the sensor portion along an edge of the display portion.

Figure 17:
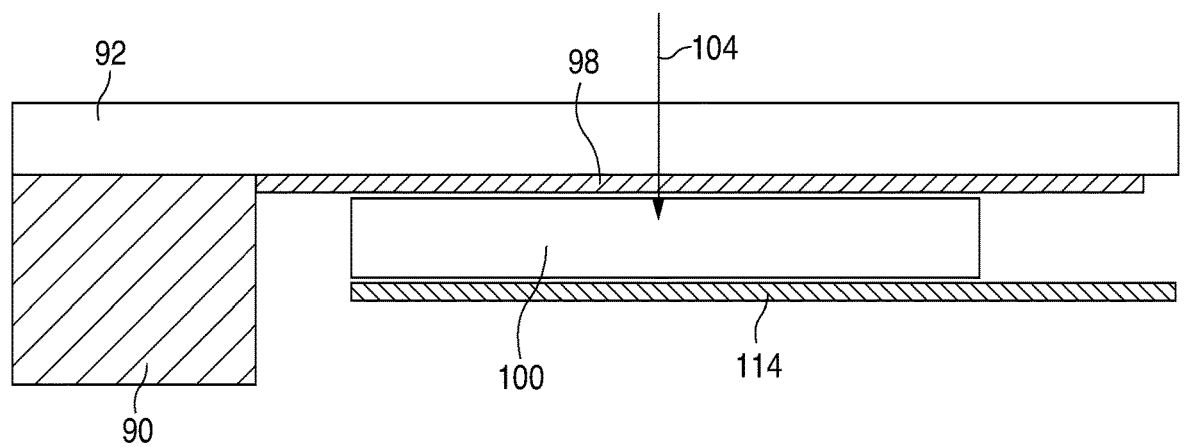

FIG. 17 is a cross-sectional view of an integrated display/sensor showing conductive traces electrically coupled to the bottom portion of the detector element.

Figure 18:
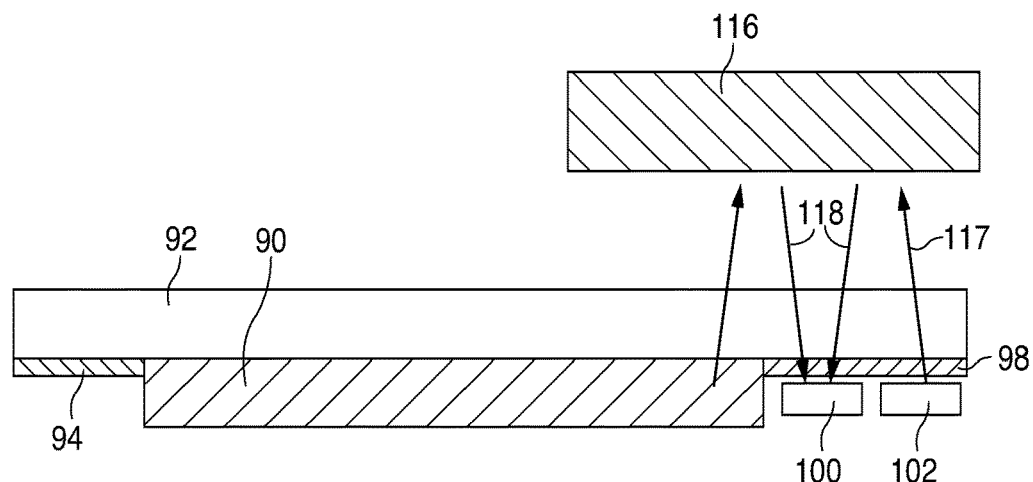

FIG. 18 illustrates the device of FIG. 15 emitting light that is reflected and absorbed by a body part, where the reflected light is detected to create a sensed image of the reflected/absorbed light to authenticate the user.

Figure 19:
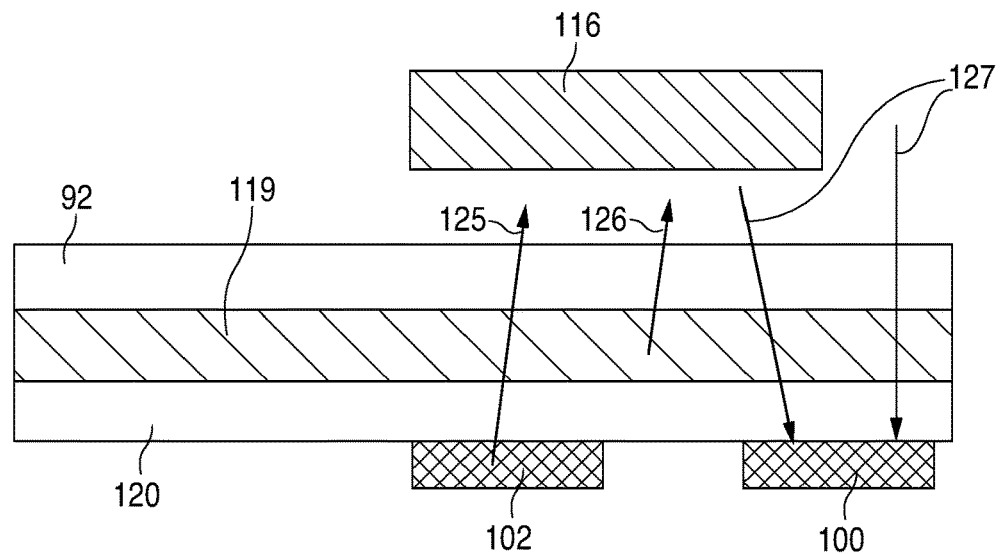

FIG. 19 illustrates another embodiment where the display area is partially transparent, and the sensor receives light from the body part through the display area.

Figure 20:
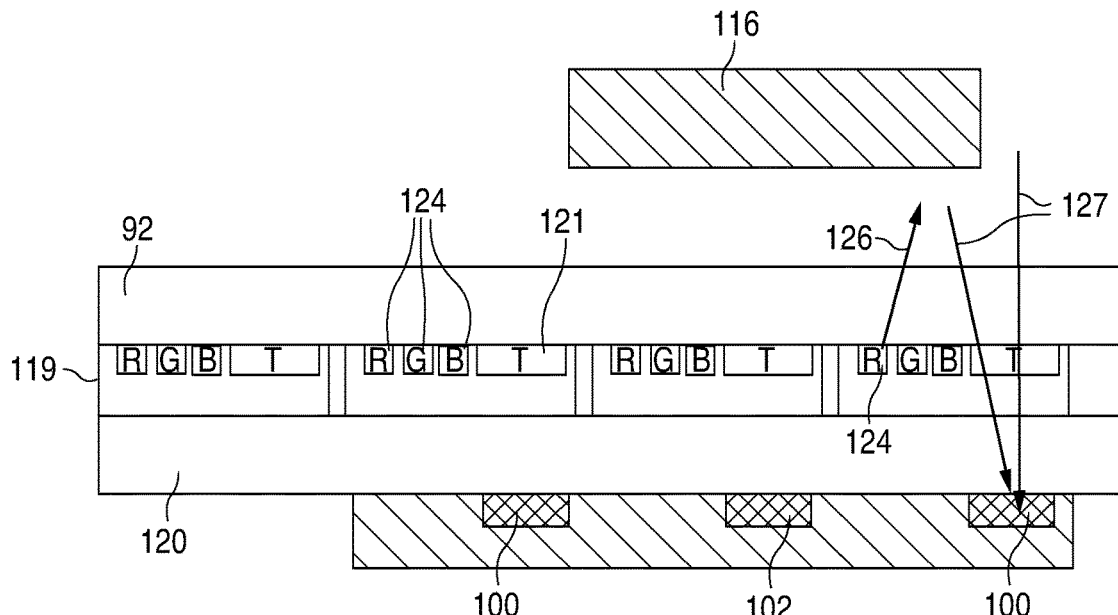

FIG. 20 is a cross-sectional view of an example of the embodiment of FIG. 19 where the display portion has distributed transparent areas through which reflected light from a body part passes for sensing by a detector array below the display portion. The display pixels (e.g., red, green, and blue sub-pixels) may provide the light source for the detector array or the light source may be a separate light source, such as an IR emitter.

Figure 21:
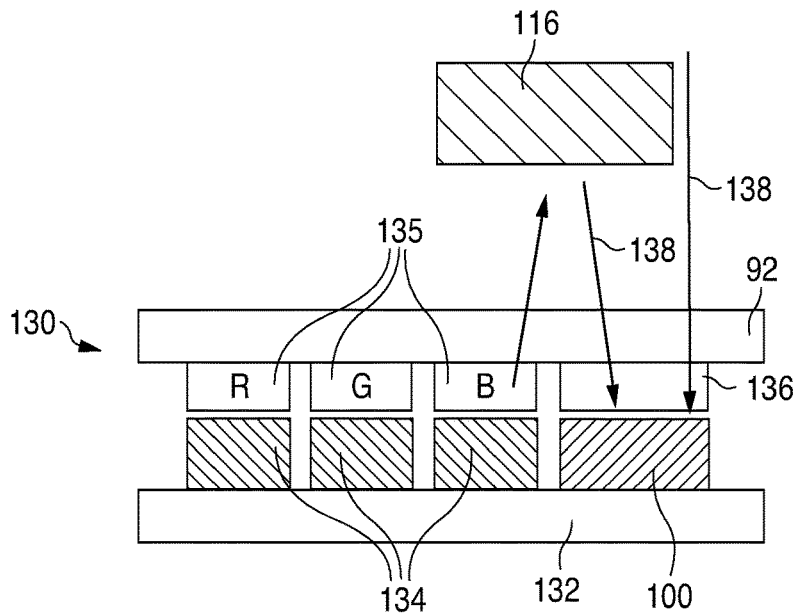

FIG. 21 is a cross-sectional view of another embodiment where red, green, and blue OLED sub-pixels are formed on a top substrate, and one or more photodiodes are formed along with thin film transistors on a bottom substrate for detecting reflected light from a body part, while the thin film transistors control the display pixels.

Figure 22:
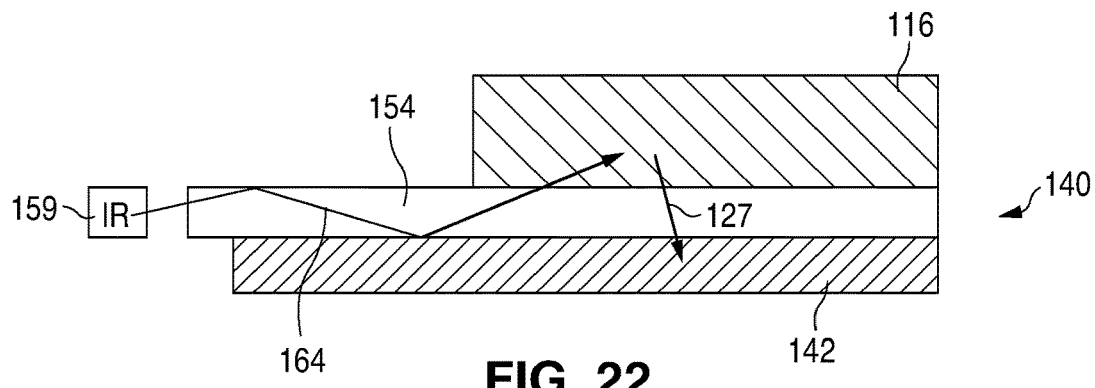

FIG. 22 is a cross-section view of another embodiment where an IR emitter, such as one or more IR LEDs, is optically coupled to an edge of the display glass of a display, acting as a light guide, and where the display glass emits the light for reflection off a body part in contact with the glass. The light may be detected only in an area laterally spaced from the display area or may be detected by photodetectors distributed within the display area.

Figure 23:
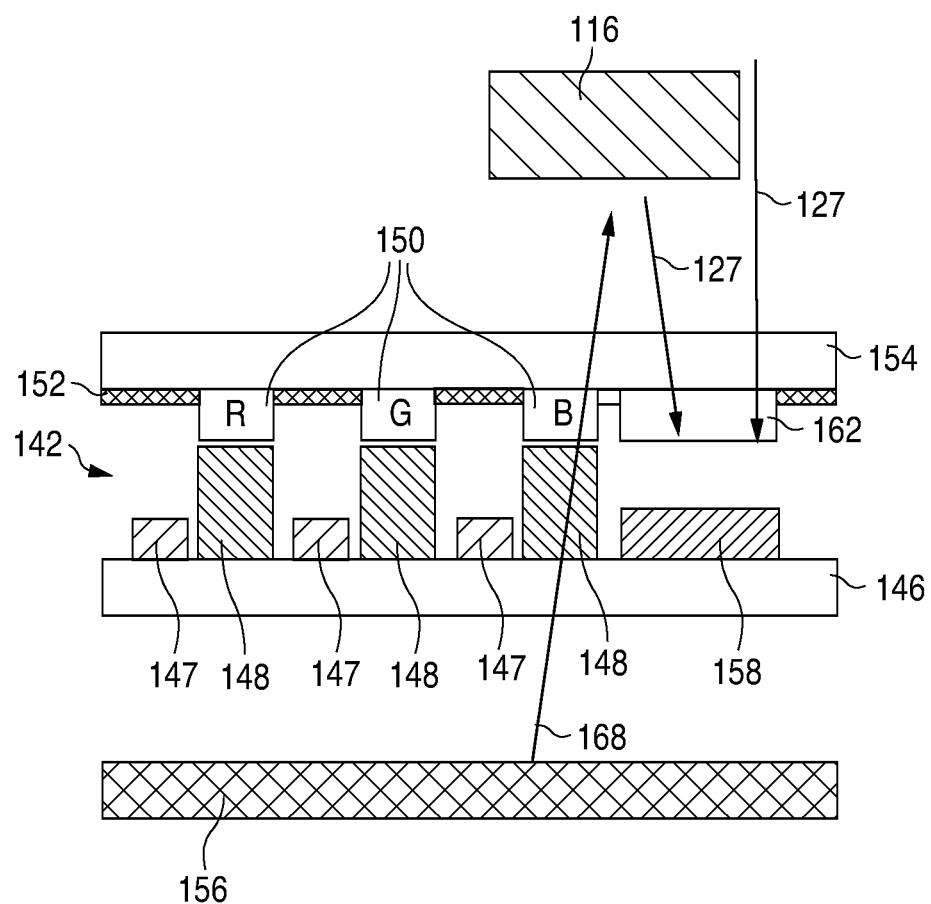

FIG. 23 is a cross-sectional view of another embodiment where liquid crystal pixels are formed on a transparent substrate (e.g., glass) along with photodiodes, where light from a backlight passes through the liquid crystal layer and is reflected off a body part for detection by the photodiodes.

Elements that are the same or equivalent in the various figures are labeled with the same numeral.

DETAILED DESCRIPTION

Various types of bio-sensor devices are described that emit light of certain wavelengths and detect, using image capture, the absorption of the light by a person's body part in contact with (or close to) the light emission window. Other uses are described.

Figure 1:
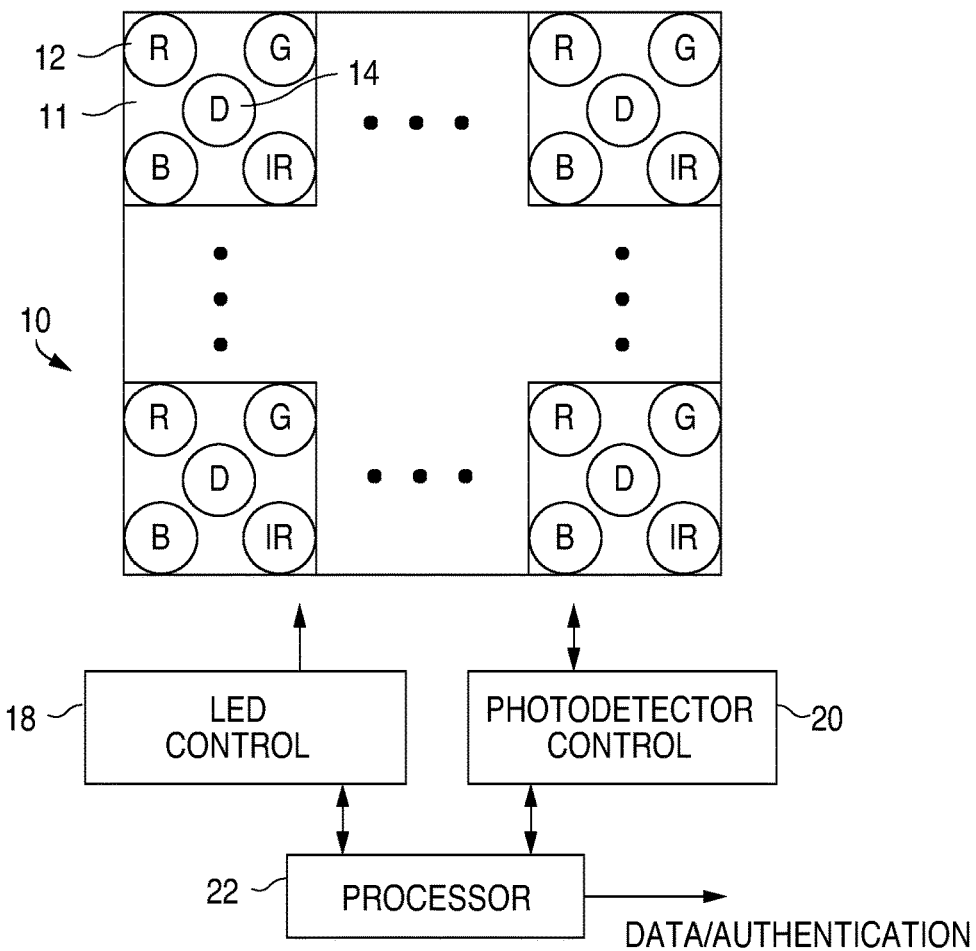
FIG. 1 is a top down view of a high resolution light emitter that may emit selected wavelengths of light in selected areas, where the device also includes an array of photodetectors within each multi-wavelength pixel area to sense light absorption from a person's body part contacting the light emitting surface.

FIG. 1 is a top down view of a bio-sensor device 10 having a size suitable for the body part reflection image to be captured. In one embodiment, the device 10 is only large enough to detect a finger touching its surface.

The device 10 comprises an array of pixels 11 formed by micro-LEDs 12 or other light sources, such as vertical-cavity surface emitting lasers (VCSELs). Such lasers are considered a subset of light emitting diodes. The LEDs 12 may be different kinds that emit different peak wavelengths of interest, or the LEDs 12 may be the same kind (e.g., UV LEDs) with different phosphors to emit the different wavelengths of interest. In the example shown, the LEDs 12 in a single pixel 11 include red R, blue B, green G, and IR-emitting LEDs. Different wavelengths penetrate the skin by different amounts; shorter wavelengths (blue, green) penetrating less deeply into the skin than longer wavelengths (red, infrared). In another embodiment, the device 10 is only intended for a particular function, such as detecting blood flow in a finger, and the LEDs 12 only emit a single narrow band of wavelengths for the particular function, such as red or IR. Each pixel 11 also includes a broadband photodiode 14 or other type of photodetector. LEDs 12 emitting different wavelengths may be separately energized, so the output of the photodiodes 14 can be correlated to the wavelength emitted by the energized LEDs 12. The resolution of the device 10 may be the same as a high resolution display.

LEDs of any one peak wavelength within the pixel array may optionally also be sequentially illuminated, with one or more detectors from within the pixel array concurrently being read, to eliminate cross-talk so as to enable further enhancement of the resolution of the image obtained by digital processing. For example, such sequentially illumination enables enhanced distinguishing of the location of absorbing features (e.g., blood vessels) within the body part from locations which are merely scattering but not absorbing the light. Additionally, the detector(s) being read may only be those proximate to the illuminated LED so that the sampled body part area is highly localized.

The LEDs may be OLEDs or inorganic LEDs.

Alternatively, the various color pixels may be formed by a liquid crystal display (LCD). A typical LCD uses a white light backlight having a broad range of wavelengths. Color filters, such as red, green, blue, and IR filters, form sub-pixels and are positioned behind a controllable liquid crystal layer. The liquid crystal layer effectively has a light shutter for each sub-pixel location. By controlling the light shutters, the different colors in each pixel are controlled. The photodiodes 14 may then be formed in a transparent laminated layer over the top of the LCD layer or below the LCD layer.

In either embodiment, the photodiodes 14 and light emitting pixels are on the same side of the person's body part to be analyzed, so that the photodiodes 14 detect an image of the reflected light, such as for detecting the absorption of light by the person's skin. This is in contrast to known devices that detect the amount of light that passes through a person's body part. The image of the reflected light corresponds to an image of absorbed light, since localized absorption in the body part being detected is basically determined by detecting differences between the reflected light received by different photodiodes 14. Such differences can be used to map the absorption pattern and compare it to a stored absorption pattern. Accordingly, the absolute magnitudes of the reflected light may vary based on the body part being sampled, any ambient light, current to the LEDs, etc., but the differences in the light reflection magnitudes will still correspond to the absorption pattern within the body part.

An example of an array of pixels 11 for a combination fingerprint detector and blood vessel location detector may be an array that is 2 cm×2 cm and contains 800 pixels 11. The resolution may be as little as 0.25 mm. Such an array size can be incorporated in a smartphone or other handheld device for authentication of the user using the two different tests.

An LED controller 18 controls the energization of the LEDs 12 using, for example, row and column addressing, and the photodiodes 14 are controlled by a photodetector controller 20. A processor 22 provides overall control of the controllers 18 and 20 and detects the outputs of the various photodiodes 14 for further processing, depending on the desired function. In one embodiment, the processor 22 controls the device to detect a fingerprint as well as the location of blood vessels in the finger, a pulse, and components in the blood. Multiple images may be obtained, like a video, for analyzing blood flow. The processor 22 may compare the data to stored information in a memory for authenticating the user or may use the data for medical analysis.

In one embodiment, the LED controller 18 rasters or otherwise spatially sequences the illumination of the LEDs whilst the photodetector controller 20 captures a sequence of images corresponding to the multiple distinct illumination states. The processor 22 may process the sequence of data to compensate the captured images for scattered light, thereby increasing the resolution of the combined image formed by absorbing features within the body part in contact with the device.

The entire device 10, including the processor 22 and controllers 18/20, may be formed as a single modular device that only requires power leads and data leads.

Different sections of the pixel array, or ones of the pixels 11, may be separately energized to reduce cross-talk between photodiodes 14 and LEDs 12 from different pixels 11. Ideally, the body part is in direct contact with the device 10 for minimizing scattering of the impinging and reflected light to obtain the highest resolution image. Focusing and directional optics may also be used to further improve resolution.

Figure 2:
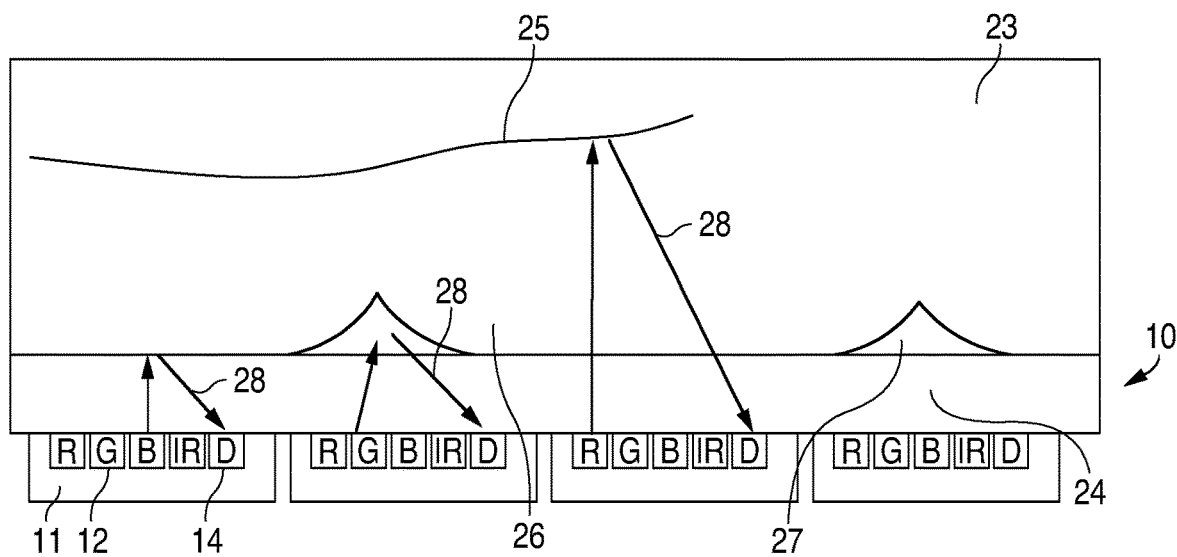
FIG. 2 is a cross-sectional view of the device of FIG. 1 showing a person's finger placed on the light emitting surface for detecting a fingerprint, blood flow, hemoglobin in the blood, or other characteristic for authentication or medical diagnosis.

FIG. 2 is a simplified cross-section of the device 10 of FIG. 1 showing a person's finger 23 in direct contact with a protective glass cover 24 of the device. A blood vessel 25 in the finger 23 is also shown. Due to the finger 23 having an index of refraction (e.g., 1.5) much higher than that of air, yet similar to the index of the glass cover 24, the fingerprint ridges 26 (directly contacting the glass) and the fingerprint valleys 27 (separated from the glass) will cause different amounts of light reflection 28 in those areas. The valley areas will reflect a relatively high percentage of light from the glass surface due to TIR at the glass/air interface, while the ridge areas will absorb a relatively high percentage of the light. Due to the high resolution of the photodiodes 14, some photodiodes 14 will be located under the valleys 27 and others will be located under the ridges 26, so the image of the fingerprint is detectable by the processor 22 (FIG. 1) and can be correlated with a stored fingerprint for authentication of the user.

The glass cover 24 may comprise an inorganic glass, a crystalline material such as sapphire, a glass ceramic, or a polymer.

Ways are known to thwart fingerprint detectors. As an added assurance against fraud, the processor 22 also processes the photodiode 14 data to determine patterns of low wavelength (e.g., red, IR) absorption consistent with blood vessels in the finger. The light enters the finger a certain distance via the fingerprint ridges. The shape and locations of blood vessels relative to a fingerprint are unique among individuals and is very difficult to fake. Such data is correlated to stored data for authentication. For example, the user performs an initial baseline detection where the combination fingerprint pattern and blood vessel pattern is detected and stored. For authentication, if a new detection substantially matches the baseline pattern, the user is authenticated. Other blood data may also be obtained for medical analysis. FIG. 2 shows the light reflectance 28 at the skin depth of the blood vessel 25, where the absorption of red/IR light is higher at the location of a blood vessel compared to areas of the finger not including a blood vessel within a target depth. A map of the detected blood vessels (in conjunction with or separate from the fingerprint pattern) can then be made by the processor 22 and compared to a stored map of reference blood vessels.

The photodiode 14 signals may be subtracted from each other by the processor 22 so that the differences correlate to absorption of the wavelength of interest. The differences in the signals output by the high resolution photodiodes 14, rather than just their absolute values, allow common-mode rejection of the light directly received by the photodiodes 14 from the LEDs, thus greatly increasing the signal-to-noise ratio.

Generally, the array of photodiodes 14 across an extended area allows for the device 10 to act as an image capture device for items of appropriate contrast in contact or close proximity to the glass cover 24. Accordingly, in the case that a body part such as a finger, palm, wrist or face is in contact with or in close proximity to the glass cover 24, the device 10 may be used to capture beneficial bio-authentication and bio-metric data such as a fingerprint, shallow sub-dermal bio-authentication data such as a blood vessel pattern, facial and other skin tone information, and the presence of skin resident pathogens.

Further, the pixel array may simply be used to detect the presence and motion of one or more fingers or other body parts in contact with or in close proximity to the glass cover 24, thereby allowing the array to be used to sense a variety of gestures or as a touch screen or simple "button" without the requirement for further dedicated touch sensing arrays, mechanical buttons, or discrete gesture subsystems.

Additionally, by sequencing the LEDs 12 of different colors, spectroscopy of the body part may be performed, yielding optically-gathered biometric data. In the case that the wavelengths penetrate the skin to some extent, sub-dermal biometric data may be obtained. For example, red and green can both be used to detect blood flow, blood vessels, and ascertain heart rate, and the combination of red and infrared of appropriate wavelengths may be used to ascertain blood oxygenation.

Different wavelengths penetrate the skin by different amounts; shorter wavelengths (blue, green) penetrating less deeply into the skin than longer wavelengths (red, infrared). Accordingly, by scanning across the pixel wavelengths, images sampling different depths of the dermis may be obtained. The data from the different images may then be subtracted from each other to yield additional resolution. For example, a blue image capturing superficial data may be subtracted from a red image capturing both superficial and sub-dermal data so as to reveal only sub-dermal data.

Extending the range of wavelength response allows even more information to be gathered. By mixing or adding additional pixels with responsivity in either higher or lower frequencies, additional functions such as pathogen detection, UV exposure, hydration, and body chemistry can be ascertained. In some cases, UV may be used to detect fluorescent components in the blood or skin.

Additionally, by capturing a sequence of images (i.e., a video), the migration of pulses of blood along a vessel can be obtained, providing further biometric data such as heart rate, blood pulse wave velocity from which blood pressure may be inferred, cardiac output, stroke volume—either directly, or by inference. The sequence of images may also be used to observe blood flow and to deduce that the body part being examined truly comprises a live body part and does not comprise an attempt to fake a bio-authentication event, such as through use of a spoof material sample or a detached or deceased body part. Likewise, the combinatory use of LEDs generating various colors together with the photodetectors can provide, for example, the identification of materials applied to a human finger which possess a copy of a fingerprint but at the same time show physiological validation. This "video" capability can then help thwart fingerprint spoofing by conformal materials.

In the case of capturing and processing an extended sequence of images, compensation may need to be provided for the motion of the subject during the video capture. In this case, motion of the superficial image captured with, for example, blue, green or other appropriate light source can be used to track the motion of the subject during video capture and can be used to compensate for motion in the captured sub-dermal images captured, for example, with red or infrared light.

Given that light penetrating into the finger is subject to variations in backscatter and reflection based on the structure in the finger, detection of the fingerprint will be best from light which penetrates least into the finger such as blue light. But a fingerprint can likely be read with a broad range of visible and near infrared wavelengths.

Using longer wavelengths, sub-dermal images can be taken. For example, using an illumination wavelength and power which allows penetration of 2-3 mm or more into the dermis will allow light to penetrate to a sub-dermal region in which capillaries and veins can be found. Given that a blood vessel will be coincident with fingerprint ridges and valleys, the image collected from the blood vessels will likely also be impacted by the presence of the fingerprint ridges and valleys. Accordingly, the presence of the fingerprint ridges and valleys may both enhance the specificity of the layers used for recognition or can be removed from the image of the vessels. In one instantiation where it is desired to remove the fingerprint, a technique of simply subtracting the image of the fingerprint as captured by shorter wavelength light as previously discussed can be deployed. Alternatively, this may be done via image processing, such as by filtering or other techniques having similar impact. The impact of the fingerprint may also be minimized by setting up the detector array such that the focal point of that detector is essentially solely or largely sub-dermal, such as by the inclusion of optics in the system (shown in later figures).

Also, by detecting both the fingerprint and blood vessel image, the orientation of the finger on the device may be random, since the fingerprint image may provide a reference for the blood vessel image. Therefore, the images relative to each other can be accurately compared to stored relative images irrespective of the finger's position on the device.

Figure 3:
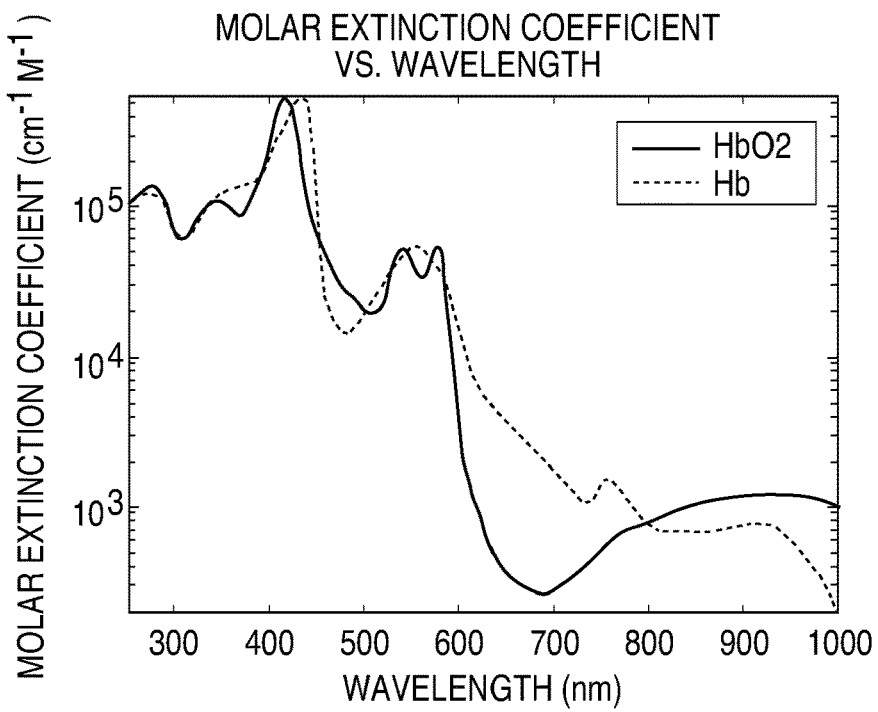
FIG. 3 illustrates a correlation of light wavelengths vs. absorption for hemoglobin and oxy-hemoglobin in the blood, which may be used by a processor in the device of FIGS. 1 and 2 to determine the concentration of such components in the person's blood.

As an artifact of this bio-authentication methodology, significant physiological information can simultaneously be extracted. By studying the image of the blood vessels captured under different illuminations, it is possible to perform a spectroscopic analysis of the tissue directly under the sensing area from which the chemistry of the blood, of interstitial fluids, or of tissue can be performed. For example, by studying the image under two different wavelengths such as 680 nm and 850 nm over which hemoglobin and oxy-hemoglobin have different changes in extinction coefficient (FIG. 3), it is possible to get a measure of blood oxygen saturation, SpO2. By extension, by studying images captured under appropriate illumination wavelengths, blood glucose, red blood cell count, white blood cell count, blood CO2, and other blood and interstitial fluid solutes can be detected.

In all of the above configurations, the impact of ambient light may need to be accounted for. Specifically, in the case of studying a thin body part such as a finger, ambient light may propagate through the finger to the detector array, interfering with the received signal or image. Accordingly, the impact of ambient light may need to be accounted for. Ambient light may comprise an essentially steady-state light source such as sunlight or a modulated light source such as incandescent lighting or modulated LED lighting. The portion of the detected optical signal originating from ambient light may be quantified by sampling the detector array first with the array light source in the "off" state. This signal may then be subtracted from the signal that the detector array subsequently captures when the array light sources are in the "on" state so as to deduce the signal relating only to the illumination by the array light source. Additionally, since all the photodiodes 14 may detect the same amount of ambient light, subtracting the common-mode signals cancels out the ambient light.

This method of correlated double sampling can further be enhanced by both the photodetector configuration and the option for multiple photodetectors in each pixel. This "ambient light rejection" can be facilitated by modulating the array light source and array detector sampling times at a frequency much higher than that of any modulation of the ambient light. The frequency of any ambient light modulation may further be detected by the detector array itself.

Whilst the above describes an instantiation utilizing micro-LED displays, a functionally equivalent modality can be achieved through the integration of an extended array of detectors integrated into any other display of appropriate resolution, such as an OLED display or an active-matrix-LCD display. Specifically, if the display includes integrated semiconducting elements such as amorphous silicon, polycrystalline silicon, or organic semiconductors, a photodiode array may be formed in the display using substantially similar semiconducting processing, hence with minimal additional processing cost and higher resolution.

A functionally equivalent modality may also be achieved with a separate extended array of detectors in, for example, an optical module, a chip on glass (a chip attached directly to a cover glass), or a chip on display (a chip attached directly to a display glass). Such a module, chip on glass, or chip on display may be integrated directly with a display, or may comprise a stand-alone array; and may comprise its own illumination sources, or may be arranged so as to utilize external light sources, such as from a display, or any other appropriate existing pixelated, uniform, side, point, or other illumination sources.

The extended array of detectors may comprise an integrated sensor array such as a CMOS image sensor, and may have optics integrated as depicted in FIG. 4, described later. The module cover glass itself may optionally be fully or partially coated with optically enhancing, optically filtering, or optically blocking layers, anti-reflection coatings, and the like.

Such a module could operate as an integration point for multiple human interface and physiological enhancements to the end application. Features such as, but not limited to, an optically-functioning on/off or other "button" on consumer devices, gesture recognition for high level functions such as pinch, zoom, scroll, joystick, trackball, signature, for example, can be added to the existing operation via algorithms or software.

An integrated or stand-alone sensor module may also be enhanced with a pressure sensor or pressure-sensing array to provide an additional mechanical button action. A laminated capacitive sensor array layer may also be integrated from which the occurrence of a "touch" event and the associated force of the touch event may be determined. Determination of the force of a touch event may also be used as a feedback to the consumer of a touch event being of a magnitude not optimized to optimal bio-authentication or bio-metric data. For example, pressing too hard on the module may restrict blood flow to the capillaries thereby impacting the signal received therefrom.

An integrated or stand-alone sensor module may further be bonded directly to a display or cover glass via an optically transparent adhesive such as an epoxy, a silicone, an acrylic or a low-temperature melting glass such as a frit glass or compound semiconductor glass. In this case, bonding may comprise an adhesive extending across the entire interface of the module cover glass and the display glass. Alternatively, adhesive may only be dispensed over a portion of the interface (e.g., at the edges), and the majority of the module cover glass and display glass may simply be in contact or close proximity.

FIG. 4 illustrates another embodiment, where the light sources 30, such as LEDs emitting the same or different wavelengths, are located only around the outer edges of a light guide 32, which also serves as the protective cover. The light is coupled into the edge portions of the light guide 32, such as by embedding the LEDs in the light guide 32 or otherwise coupling the light into the edges. The light is carried to all areas of the light guide by TIR and exits through only the top surface of the light guide 32.

If the body part is to be in direct contact with the light guide 32, the light will be naturally extracted from the light guide at the points of contact by the body part due to the skin having an index of refraction similar to that of the light guide. If the body part to be detected may be spaced from the light guide 32, the light guide 32 may have light extraction features, such as molded micro-reflectors (prisms), which direct the light upward and mix the light. Using such distributed micro-reflectors in a light guide for backlighting is well known. Accordingly, the light from the energized LEDs may be substantially uniformly emitted upward into the body part in contact with or proximate to the light guide surface. There is little or no downward light emitted by the light guide 32. Much of the light guide 32 is transparent so that light reflected back from the body part passes through the light guide 32. Such a design using a light guide is relatively inexpensive compared to integrating IR LEDs and photodetectors into a display screen along with the display pixel LEDs. Further, the resolution of the photodetector array is independent of any display pixel array and thus can be made a higher resolution.

Optics 34 may comprise focusing micro-lenses that focus reflected light from only a certain distance into the body part onto a photodiode array 38. The optics 34 may also limit the incoming light from the body part to only a narrow angle normal to the light guide to reduce cross-talk and to better map the features of the body part being analyzed. The photodiode array 38 may be a CMOS image sensor, a CCD image sensor, or any other image sensor.

A light blocking wall 40 may be used to block direct light from impinging on the photodiode array 38. The module may include an opaque heat conductive enclosure 42 to sink heat from the LEDs. The control electronics of FIG. 1 may be attached to the module or separate. The module may have contact pads for soldering to a printed circuit board.

FIG. 5 illustrates the module of FIG. 4 abutting a protective transparent cover 44, such as a transparent surface layer of a smartphone or other device.

As will be described in detail later, the IR emitters in FIG. 2 may be deleted from within the display pixel array and edge-coupled into the display glass. The IR light is then uniformly spread within the display glass by TIR until it encounters skin tissue (e.g., a finger) directly contacting the display glass. At the points of contact, the light will be reflected/absorbed by the skin tissue and detected by the distributed photodiodes 14 in the display pixel array. Therefore, the body part may touch any portion of the display glass at any orientation for detection.

As shown in FIG. 6, an integrated or stand-alone sensor module may further comprise one or more electrodes 48 and 50 extending through or around the light guide 32 or located external to the module but electrically connected to the module to allow a user to be monitored electrically. For example, such electrodes 48 and 50 may be used to detect a user's electrocardiogram (ECG or EKG) or bio-impedance. The ECG signal may be used in isolation to determine heart-rate, or impending or actual medical conditions relating as determined by the form of the ECG signal. Alternatively, the ECG may be used in-tandem with an optically-derived photoplethysmogram (PPG) to determine blood pressure and other medically-important indicators. Bio-impedance may be used to determine hydration, fat content, or other vital signs. Muscular action may also be monitored electrically. All such monitors may combined in a single module.

The ECG signal may also be used as a bio-authentication signature.

Thus bio-authentication may be performed via a single modality such as fingerprint, vascular imaging, or ECG; or through a combination of multiple modalities; a form of multi-factor authentication. Given that all bio-authentication events are subject to error in the form of false positives and false negatives, the use of multi-factor bio-authentication can improve the accuracy of bio-authentication. For example, a multi-factor bio-authentication scheme may be configured to confirm an authentication event comprising positive authentication of two factors and rejected authentication of a third factor, thereby reducing the probability of a user being locked-out of a system due to a false negative—albeit at the expense of reduced security—whilst providing increased security against false positives and spoofing by requiring at least two factors to be authenticated. Alternatively, given that different modalities have different authentication times, a multi-factor authentication scheme may be configured to provide a first, fast, low security authentication based on a single, fast authentication factor, and one or more subsequent levels of increasing security authentication over the extended time period required to gather and process the additional slower authentication factors.

As shown in FIG. 7, the module may be further augmented with an integrated gas sensing element 54. The gas sensing element 54 may instead be a discrete proximate device. Use of a high-specificity, high-directivity gas sensor, such as an appropriate electrochemical sensing element, may be used to detect current or impending medical conditions, much as a dog can smell illness in people. Such data can be used in isolation, or in conjunction with the optical and electrical data outlined above to provide a more complete context in which the data can be interpreted, thereby resulting in a more (statistically) accurate medical diagnosis or general health/wellness diagnosis.

Use of a complementary gas sensing element 54 may also be used in a bio-authentication application. A fingerprint spoof sample may comprise fingerprint reproductions into or onto organic materials such as wood, glue, putty, acetate sheets, and the like. Such materials mostly emit volatile organic compounds—especially in the short time after formation or curing. Additionally, humans all emit volatile organic compounds (VOCs) through the skin and sweat. Therefore, a contact or close-proximity fingerprint or other bio-authentication event in which the gaseous environment at the contact point is sampled at substantially the same time as the bio-authentication event has the opportunity to "smell" the presence of a spoof material or direct skin. Further, the particular ratios of VOCs emitted by any one individual (one's "odor") may be sufficiently distinct that it may be used as a further bio-identification factor or modality if sufficient resolution exists in the gas sensing element. Such a sensing scheme is depicted in FIG. 7 by the photodiode array 38 sensing light absorption by the fingerprint and/or blood vessel location in conjunction with the gas sensing element 54 detecting the presence of an actual human finger 23.

An integrated or stand-alone sensor module may be arranged as a compact line-scanner (single or narrow line of pixels) across which a finger can be physically scanned or swiped. This may provide the advantage of being able to scan an extended part of the finger or other body part with a reduced sensor footprint. In the case of a stand-alone sensor module, the reduced footprint can facilitate design-in to space constrained platforms such as cellphones, watches and other wearables and can facilitate reduced module cost.

The swiping action of the finger can allow the small form factor sensor to survey an extended range of body tissue. Being able to sense over extended ranges of body tissue provides the advantage that particular bio-authentication and bio-metric markers can be sampled in the specific tissue areas where the markers are the strongest or most highly defined. For example, if trying to obtain a traditional fingerprint, scanning tissue over the distal phalanges will provide the most useful information since that is a region rich in superficial skin features (ridges and valleys). On the other hand, capturing unique sub-dermal information such as finger vein identification data may prove most successful over the middle phalanges where the veins are larger, hence both easier to detect and less impacted by the application of pressure to the finger by contact with the sensor module during the bio-authentication event. Accordingly, an optical bio-authentication line scanner may be configured to optimally capture fingerprint data from the distal phalange and finger vein identification data from the middle phalange as the finger is scanned over it. The module may further sense the passage of the finger over the module and change the operation of the module during the finger scan, such as by a change in illumination source or focal length as the sensor passes under one of the interphalangeal joints.

A line array sensor may further be formed on or behind a flat cover glass, or a curved cover glass, the curve of the glass approximately matching that of the finger or a wrist. Such a sensor may then be incorporated into a wearable device such as a ring or a watch which, if networked, can be used to as a wearable device providing bio-authentication of the user. Such a device can perform a one-time bio-authentication event. It can then continuously or periodically pole the sensor array to confirm that the wearable device has not been removed and that the user is still alive. The wearable device can then confirm that the user remains bio-authenticated without having to perform any subsequent bio-authentication events. Such a device can then be wirelessly networked, for example, with phones, credit card payment systems, ATMs, cars, doors, data vaults and the like to facilitate fast user authentication. Such a modality is of particular use in the case that a bio-authentication event comprises a lengthy event, such as if it comprises an analysis of ECG signals which may require several heart beats to be captured.

As shown in FIG. 8, signals from an integrated or stand-alone sensor module may be further augmented with data from an integrated or discrete proximate contact or non-contact temperature sensor 58. A low wavelength (red or IR) filter 60 may cover the sensor 58. Temperature data may be used as a standalone biometric or may be used to provide further context within which other biometrics are interpreted.

FIG. 9 shows an embodiment where the control circuitry and photodiodes are integrated in a sensor chip 62, and the focusing optics 64 is formed directly on the photodiode array for more precise focusing. The focusing may be within a certain distance into the body part contacting the light guide 32. The edge-coupled LED light sources 30 are also shown. The resulting module is very thin and easily incorporated into various applications.

FIG. 10 is a top down view of one embodiment of the sensor chip 62 and optics of FIG. 9. Each plenoptic lens 68 overlaps an arrayed group of photodiodes 14, and a micro-lens 66 may cover each photodiode 14. The pitch between photodiodes 14 may be less than 0.25 mm to form a compact array. In this scheme, the array of photodiodes 14 (detector pixels) under each plenoptic lens 68 results in one macro-pixel which has a resolution of 0.25 mm. Each micro-lens 66 over each photodiode 14 improves light capture and may provide directionality. Each plenoptic lens 68 in the example overlaps about 16 photodiodes 14. The plenoptic lenses 68 may focus at different depths and be directional to gather more information about the reflected light from the body part. The various lenses may be formed by molding a transparent sheet and laminating the sheet over the photodiode array, or may be formed by direct molding over the photodiode array. Although hemispherical lenses 68 are shown for simplicity, the lenses may be any shape suitable for focusing. The chip can be affixed to the back of any light guide glass. In another embodiment, the optics is spaced from the photodiode array with a spacer. Reference photodiodes 69 may be located outside of the plenoptic lenses 68 for detecting ambient light. System logic 70, for processing the detected signals, is formed on the same chip as the photo-diode array for compactness and improving the signal-to-noise ratio. The logic may include analog-to-digital converters and digital processing circuitry.

FIG. 11 illustrates the module of FIG. 10 augmented with LED light sources 72. The light sources 72 may inject light into an overlying light guide to spread the light over the photodiode array, as previously described. Light reflecting from the body part passes back through the light guide to the photodiode array. In another embodiment, a light guide is not needed since the module may be small (e.g., less than 2×2 cm) and the light from the LEDs light sources 72 is scattered within the body part and reflected onto the photodiode array.

Since LED performance degrades over time, the photodiodes 14 may also be used to compare the LED light output against a baseline and provide feedback to the LED energizing circuitry to achieve the baseline performance.

Although the embodiments above comprise spectroscopic analysis performed by an array of broad-band detectors in conjunction with narrowband emitters, the functionality could also be implemented through the use of wavelength-specific detectors such as detectors with optical filters on them or in their optical path, in conjunction with broadband emitters such as phosphor-converted white-LEDs.

FIG. 12 identifies various possible uses of the modules described herein.

FIG. 13 is a flowchart identifying basic steps performed by the various modules according to one embodiment of the invention.

In step 80, an LED display panel, light guide panel, or other light source is arranged relative to a photodetector array to form the bio-sensor.

In step 82, the output window of the bio-sensor is touched by a body part for analysis. A touch sensor, or a light shadow sensor, may be incorporated in the device for detecting when a body part is over the output window to start the image detection process.

In step 84, the LEDs are energized to apply the desired wavelengths to the body part to detect localized light absorption by the body part for fingerprint detection, blood vessel detection, pulse, etc. The LEDs may be energized concurrently or sequentially. If the LEDs are energized sequentially, the photodetectors may be selectively read so as to better associate absorption of the light with the locations in the body part proximate to the energized LED. The sequential illumination may be in any pattern.

In step 86, the signals from the photodetector array are scanned, such as by column and row, to detect the relative magnitudes of the detected light across the array to effectively obtain a detailed image of the light absorption by the body part.

In the event that the LEDs are sequentially energized, the method may then loop back to step 84 after each energization to provide additional spatial absorption data.

In step 88, the raw data is processed by the module's processor to obtain results, such as authentication of the user, medical analysis, etc.

Various other embodiments are disclosed below, including embodiments where the photodetectors and light sources are located outside of a display area so as not to affect the display portion itself. Thus, the display portion may be generally conventional. The photodetectors are covered by the same glass that covers the display screen. The light emitted for the biosensor function may be from an edge portion of the display or from a light source separate from the display portion.

Also described are embodiments, where the display portion includes distributed transparent portions through which light reflected by a body part passes and is detected by an underlying photodetector array.

FIGS. 14-18 illustrate an integrated display and optical sensor, where the sensor is laterally spaced from the display portion but uses the same display glass or cover glass. The display area 90 includes an array of red, green, and blue pixels that are addressed to display any image. The device may be a smartphone display. The display area 90 is covered by a thin display glass 92 (or other type of light passing panel), which may include a touchscreen sensor layer.

The active area of the display area 90 is surrounded by a black ink 94 for aesthetic purposes. The ink is typically black but may be any color.

Next to the display area 90 is a sensor area 96 that uses the same glass 92. In the event that the black ink 94 is opaque to IR, the sensor area 96 is either not covered with an ink or covered with an IR ink 98 that passes IR. The IR ink 98 may appear black.

One or more optical detector elements 100, such as photodiode dies, are mounted under the IR ink 98 such that they may detect light passing through the IR ink as shown in FIG. 16. An IR emitter 102, such as an IR LED, is energized to apply light to a body part contacting the glass 92 above the sensor area 96. Other wavelength LEDs, such as red, may also be in the sensor area 96, depending on the biologic characteristic to be detected. Assuming the body part is a finger, the IR light or red light is partially reflected off the surface of the finger and also enters the finger, particularly where the crests of the fingerprint contact the glass 92. Some of the light is absorbed by blood and blood vessels, or by certain components in the blood, and the pattern of the absorption is detected, as previously described.

In another embodiment, the light emitted by the sensor area 96 may be white light, and the detector elements 100 detect an image of the reflection of the white light off any object, including a body part or printed code, in front of the sensor area 96.

By laterally spacing the detector elements 100 and the IR emitter 102 from the display area 90, the display area 90 is not affected by the sensor area 96. Therefore, the display area 90 can have a very high resolution array of pixels.

Optics may be incorporated into the optical path of the detector. For example, the optics may be molded over or mounted to the detector die. Alternatively, optics may be molded onto or otherwise mounted to the display glass 92 or the IR ink 98. Optics may also optionally be etched into the display glass 92. Optical filters such as organic dyes, dielectric filters, or metal-dielectric filters may also be placed directly on the photodetector dice, on the display glass 92, or on any other appropriate element in the optical path. The detector may comprise an array of pixels or a focal plane array.

FIG. 16 illustrates a detector element 100 in more detail. Reflected light 104 passes through the IR ink 98 and is detected by the detector element 100, which may be a single detector element or an array of detector elements to generate a high resolution image of the reflection/absorption of light by the body part, such as a finger.

In another embodiment, the LEDs in the display area 90 supply the light that is reflected off the body part, since there will be some scattering of light within the body part that reaches the detector elements 100.

An advantage of the device of FIGS. 14-18 is that the sensor area 96 does not affect the construction or operation of the display area 90, which may be a smartphone display.

The sensor area 96 may be used to detect the user's fingerprint and/or blood vessel pattern for authentication.

As shown in FIG. 16, electrical interconnection to the detector element 100 may be via conductive traces 106 and 108 deposited onto the IR ink 98 and appropriate interconnects 110 and 112 (e.g., a conductive adhesive, solder, etc.). The conductive traces 106/108 may alternatively be deposited directly onto the glass 92, and patterned IR ink 98 may be deposited on top of them. The conductive traces 106/108 may comprise, for example, conducting oxides, conducting organic materials, semiconductors, metals, or mixtures thereof. The interconnects 110/112 may comprise, for example, solders, metals, conducting pastes, conducting films, or anisotropic conducting elements. The detector element 100 may comprise a stand-alone photoreceptor or a 2-dimensional or linear array thereof, or may comprise an element integrating one or more photoreceptor elements such as photodiodes with analog electronic circuitry and optional analog-to-digital convertors, digital control logic, digital-to-analog circuitry, and processing circuitry. The detector element 100 may comprise a CMOS image sensor or similar device.

A back cover 113 is also shown in FIG. 16.

As shown in FIG. 17, electrical connection to the detector element 100 may also be made independently of the glass 92, for example, by a flexible PCB (flex circuit), PCB, ribbon connector, wire assembly or any other appropriate element connected to the backside of the detector element 100. A metal trace 114 is shown in the example. Electrical connection to the backside of the detector element 100 may also be made via spring connectors or other similar interconnect schemes. In such schemes, the detector element 100 may comprise technology such as that used in back-side illuminated (BSI) CMOS Image sensors.

One or more light emitting devices such as an LED or a VCSEL may also be mounted to the glass 92. The light emitting device and the detector element 100 may be mounted to the glass 92 in a similar fashion. Optics may be incorporated into the optical path of the light emitting device. For example, the optics may be molded over or mounted to the emitter. Alternatively, optics may be molded onto or otherwise mounted to the display glass 92 or the IR ink 98. Optics may also optionally be etched into the display glass 92. Optical filters such as organic dyes, dielectric filters, or metal-dielectric filters may also be placed directly on the photodetector dice, on the display glass, or on any other appropriate element in the optical path. In this case, light is emitted from the light emitting device through the IR ink 98 and is incident on a partially reflective body (such as a user's face, hand, or finger) above or in contact with the display glass 92. As shown in FIG. 18, the emitted light 117 from the IR emitter 102 is reflected back (light rays 118) from the body part 116 and detected by the detector element 100. Alternatively, the display itself may be used as the emitter, and the detector element 100 may simply detect the reflected light from the display.

Whereas the examples given above comprise the detector element 100 being positioned behind an IR ink 98, the detector element 100 may be positioned on the glass 92 in the absence of any ink.

In the examples above in which emitted light is required as part of the sensing scheme, double-correlated sampling at time points with the light emitter on and off can help differentiate between the reflected signal and the background light.

FIGS. 19 and 20 illustrate a partially transparent display 119, such as a partially-transparent OLED display, with one or more optical detector elements 100 mounted to the backside of the display 119, such as on a backside glass plate 120. The display 119 may comprise an array of deliberately transparent areas 121 ("transparent pixels"), shown in FIG. 20, whose purpose is to provide an optical path through the display 119, thereby rendering it partially transparent. In such an example, a detector element 100, which may be an array of photodiodes or other photodetectors, mounted to the rear of the partially-transparent display 119 may optionally be aligned to the pixel array of the partially-transparent display 119 such that the photosensitive elements in the detector array lie directly below the transparent areas 121 in the partially-transparent display 119. The light reflected off the body part 16 may be from the display pixels 124 or from a dedicated emitter 102. In FIG. 19, a light ray 125 is shown being emitted by a dedicated emitter 102, and in FIG. 20, a light ray 126 is shown emitted by a red pixel 124. Reflected light 127 is shown being detected by the detector element 100.

Optics may be incorporated into the optical path of the detector element 100. For example, the optics may be molded over or mounted to the detector die. Alternatively, optics may be molded onto or otherwise mounted to the backside glass plate 120, or etched or otherwise patterned into it. Optical filters such as organic dyes, dielectric filters, or metal-dielectric filters may also be placed directly on the photodetector dice, on the display glass, or on any other appropriate element in the optical path. The detector element 100 may comprise an array of pixels or a focal plane array.

Any of the display elements may be used as a light source, and reflected light from a body part may be detected by the detector element 100. Red, green, and blue LEDs 124 (labeled RGB) are shown in each display pixel area proximate to the transparent areas 121. The display pixel array itself, typically comprising red, green and blue arrayed pixels, may optionally be augmented to include infra-red emitting pixels, ultra-violet emitting pixels, or emitting pixels of any other appropriate wavelength. In such a scheme, OLED materials emitting in the infra-red, ultra-violet or other appropriate wavelength range may be used. In the case of a micro-LED display, infra-red and ultra-violet LEDs made of for example $Al_xIn_yGa_zP$ and $Al_xGa_yN$ respectively may be incorporated as part of the red, green and blue LED pixel array; and other appropriate wavelengths may be generated by these same materials or other compound semiconductor alloys.

Alternatively, one or more separate optical emitters 102 may be mounted behind the partially-transparent display 119. Light from these emitters 102 may be transmitted through the partially transparent display 119, reflected off the external body part 116 and detected by the detector element 100. Optics may be incorporated into the optical path of the emitter 102. For example, the optics may be molded over or mounted to the emitter die. Alternatively, optics may be molded onto or otherwise mounted to the backside glass panel 120, or etched or otherwise patterned into it. Optical filters such as organic dyes, dielectric filters, or metal-dielectric filters may also be placed directly on the photodetector dice, on the display glass, or on any other appropriate element in the optical path.

Separate emitters may alternatively be mounted along the side of the display, similar to the design of FIG. 14. These separate emitters may comprise infra-red emitters, ultra-violet emitters, or emitters of any appropriate wavelength and may comprise, for example, LEDs or phosphor-converted LEDs. Alternatively, separate emitters in the end product such as a camera flash, an indicator LED, light sources incorporated into other optical communication links, or any other light source may be used as an illumination source whereby a reflected signal from a proximate body may be detected. Additionally, as previously described, the light sources may be edge-coupled into the display glass and the display glass internally spreads the light by TIR until it escapes at the points of contact of the body part and the display glass.

FIG. 21 illustrates a single pixel in a display 130, such as an AMOLED display, further comprising a semiconductor backplane 132 comprising a thin film transistor (TFT) array 134 formed in low-temperature polycrystalline silicon (LPTS), amorphous silicon (a-Si), or crystalline silicon. In such an embodiment, one or more photosensitive detector elements 100 are formed in the semiconductor backplane 132 prior to deposition of the superficial organic electroluminescent layers. The detector element 100 may comprise, for example, a photodiode such as a p-i-n photodiode. OLED material may be grown or deposited over the TFT array 134 to form red, green, and blue sub-pixels 135. Infra-red sub-pixels may also be so formed as part of the array. Optics 136 may optionally be formed or otherwise placed over the detector element 100. Such optics may comprise, for example, a lens formed by, for example a photoresist reflow process or a printing process. The one or more detector elements 100 may be used as an optical detector or detector array integrated directly into the display. Light rays 138 are also shown.

Optical filters such as organic dyes, dielectric filters, or metal-dielectric filters may optionally be incorporated over the detector elements 100 so as to produce pixels having sensitivity to specific wavelengths. For example, red, green, blue, cyan, magenta, yellow, IR, and UV absorbing dyes may optionally be placed over different detector elements so as to provide a multi-pixel detector capable of color sensing or spectroscopy. The OLED materials themselves may optionally be placed over the photodiodes; the red, green, and blue OLED materials all having different absorption spectra—hence acting as distinct optical filters.

FIG. 22 shows another embodiment of an integrated display and detector, and FIG. 23 shows a single pixel area in the display/detector of FIG. 22.

A full color display 140 includes a backplane 142 such as a TFT-LCD comprising a thin film transistor (TFT) array formed in low-temperature polycrystalline silicon (LPTS), amorphous silicon (a-Si) or crystalline silicon. The transistors may be patterned and doped amorphous silicon deposited on a transparent glass substrate 146 (FIG. 23), and the patterned conductors may be transparent, such as ITO. The array of thin film transistors 147 is formed on the glass substrate 146 along with an LCD layer 148, where the transistors 144 are turned on by conventional column and row decoders to control each LCD pixel, one of which is shown in FIG. 23.

Color filters 150, such as blue, red, and green filters are formed above or below the LCD layer 148 for forming the blue, red, and green subpixels. Infra-red sub-pixels may also be so-formed as part of the pixel. A black mask 152 is printed on the top display glass 154 to better optically separate the subpixels.

The display portion of the backplane 142 may be conventional.

A white backlight 156 is positioned below the backplane 142, and the LCD subpixels act like controllable shutters to emit selected amounts of blue, red, and green light for each pixel to generate a wide gamut of colors.

Photolithography is commonly used to form the backplane 142, and very high resolutions can be obtained.

To augment such a display with a detector, one or more photosensitive elements 158, such as amorphous silicon photodiodes, are also deposited and patterned on the backplane 142 by photolithography. The photodiodes may be a variant of the silicon transistors 147 formed in the TFT array and formed using additional masking steps. The TFT array and photodiodes may be formed in the same plane on the glass substrate 146. Suitable conductors on the substrate 146 connect the photodiodes to detector circuitry. The photodiodes may be outside the display area or distributed throughout the display area. The photosensitive elements 158 may comprise, for example, a photodiode such as a p-i-n photodiode.

As shown in FIG. 22, an IR emitter 159 or other peak wavelength LEDs are optically couple into the edge of the display glass 154, where the display glass 154 is used as a waveguide to spread the IR light 164 and emit the IR light 164 only above the photodetector element 158 away from the backplane 142. The light is extracted from the display glass 154 only at the areas where the body part 116 contacts the display glass 154, as previously described. If the body part does not need to contact the display glass, the surface of the display glass 154 may be roughened over the photodetector element 158 to extract the waveguided light. The display glass may be clear over the display portion of the pixel.

An IR filter 162 may also be printed on the bottom surface of the display glass 154 and may be planar with the RGB color filters 150.

FIG. 23 shows the backlight 156 providing the light 168 for the detector; however, the light for the detector may be coupled into the edge of the display glass 154, as shown in FIG. 22.

Optics may optionally be formed or otherwise placed over the photosensitive element 158. Such optics may comprise, for example, a lens formed by, for example a photoresist reflow process or a printing process. This one or more photosensitive element may be used as an optical detector or detector array integrated directly into the display. In such an instantiation, a light blocking layer can be incorporated between the growth substrate and the photo-sensitive element so as to block direct illumination of the photo-sensitive element by the backlight.

Optical filters such as organic dyes, dielectric filters, or metal-dielectric filters may optionally be incorporated over the detector pixels so as to produce pixels having sensitivity to specific wavelengths. For example, red, green, blue, cyan, magenta, yellow, IR, and UV absorbing dyes may optionally be placed over different detector pixels so as to provide a multi-pixel detector capable of color sensing or spectroscopy. The standard LCD color filter materials themselves may optionally be placed over the photodiodes.

In some embodiments, detector pixels may be also be arranged directly under LCD elements, such that the LCD matrix may be used to shutter the detector pixels, facilitating capture of an image by the array.

FIG. 22, the display portion operates normally to display any image or instructions, while the IR LED 159 of FIG. 22 is energized to cause the display glass 154 to emit IR light in the area of the photodetector element 158. The emitted light is reflected and absorbed by the body part 116 above or in contact with the display glass 154 proximate to the photodetector element 158, and the signal from the photodetector element 158 is processed by detector circuitry to identify characteristics of the body part 116, such as a fingerprint, blood vessels, face recognition, combinations thereof, etc. The photodetector element 158 may comprise any number of pixels depending on the resolution desired. Accordingly, all the emission for the detection is generated by a side emitting light source, such as the IR LED 159, so no display pixel area is taken up by the IR emitter.

At the point at which the glass is in contact with human tissue, the close index of refraction of the glass 154 and the human tissue is such that light is transmitted into the tissue. Light is then attenuated and back-scattered from the tissue onto the detector array from which it can be detected. A bio-authentication signature or bio-metric data can be ascertained from this detected light.

Wavelengths other than IR may be used to detect other biologic characteristics, especially for face recognition.

In one embodiment, the display portion may be high resolution for displaying a conventional image while the detector portion may include low-resolution visible light pixels for identifying the location of the detection portion under the display glass. For example, the light emitting pixels (e.g., RGB or white) in the detection portion may provide an outline of the detector area or identify simple instructions for the user. In such an embodiment, the pixels in the display portion operate independent of the light emitting pixels in the detection area. The light emitting pixels in the detector area may also serve as illumination pixels for the body part to be detected.

In all embodiments, the detection circuitry and control circuitry of FIG. 1 may be integrated into the device.

While particular embodiments of the present invention have been shown and described, it will be obvious to those skilled in the art that changes and modifications may be made without departing from this invention in its broader aspects and, therefore, the appended claims are to encompass within their scope all such changes and modifications that are within the true spirit and scope of this invention.

What is claimed is:
1. A bio-sensor device comprising:
a display portion having a light passing panel, wherein the display portion comprises a two-dimensional pixel array containing light emitting diodes emitting a first set of peak wavelengths and configured to display a full color image;
a two-dimensional array of light sources, distributed within the pixel array, configured to emit light through the light passing panel so as to be partially reflected and absorbed by blood in a person's finger overlying the display portion, the light sources being co-planer with the pixels and emitting light having at least a peak wavelength not within the first set of peak wavelengths;

a two-dimensional array of photodetectors distributed within the pixel array and arranged to detect light reflected back by a surface of the finger and the blood in the finger, the photodetectors generating first signals corresponding to the light reflected back, the photodetectors being co-planer with the pixels;

a controller coupled to the display portion and the array of light sources, the controller being configured to control pixels in the display portion to emit light of one or more peak wavelengths during a first period of time to detect a fingerprint of the finger and capture a first image of the fingerprint, wherein the array of light sources do not emit light during the first period of time, and the controller bring configured to control the array of light sources during a second period of time to detect the blood in the finger and capture a second image of the blood in the finger; and detection circuitry coupled to the photodetectors configured for analyzing the first signals to detect the fingerprint using only the pixels energized in the display portion during the first period of time and to detect the blood in the finger using light emitted by at least the array of light sources during the second period of time.

2. The device of claim 1 wherein the pixels generate red, green, and blue light, and the light sources generate infrared light.

3. The device of claim 1 wherein the light sources are laterally spaced from the pixels in the display portion.

4. The device of claim 1 wherein the light sources comprise light emitting diodes.

5. The device of claim 1 wherein the light sources comprise light emitting diodes emitting different peak wavelengths of light.

6. The device of claim 1 wherein the light sources emit light of a wavelength that is absorbed by blood vessels.

7. The device of claim 1 further comprising lenses over the photodetectors for limiting an angular range of reflected light from the finger.

8. The device of claim 1 further comprising lenses over the photodetectors for focusing reflected light from the finger onto the photodetectors from only a certain distance into the finger.

9. The device of claim 1 further comprising a non-optical sensor integrated into the device.

10. The device of claim 9 wherein the non-optical sensor comprises electrodes for touching by the finger.

11. The device of claim 1 wherein the device is configured to detect blood vessels in the finger.

12. The device of claim 1 wherein the controller comprises a processor integrated into the device, the processor controlling energization of the light source and detection of the reflected light received by the photodetectors.

13. The device of claim 1 wherein the controller comprises a processor, the processor being configured to process data from the photodetectors, compare the data to stored data, and indicate authentication of a user of the device.

14. The device of claim 1 wherein the controller comprises a processor, wherein the light sources comprise a plurality of light emitting diodes, wherein the processor is configured to control the light emitting diodes to be sequentially illuminated while signals from the photodetectors are read and processed by the processor.

15. The device of claim 1 wherein the controller comprises a processor, wherein the processor is configured to detect a light reflection image of the finger to determine areas of absorption of the light in the finger.

16. The device of claim 1 wherein the controller comprises a processor configured to process data from the photodetectors, wherein the processor detects movement of the body part for detecting a gesture.

17. The device of claim 1 wherein the controller is configured to control the array of light sources during the second period of time, while also controlling one or more pixels in the display portion to emit light during the second period of time, to detect the blood in the finger and capture the second image of the blood in the finger.

18. The device of claim 1 wherein the controller is configured to control the array of light sources during the second period of time, while also controlling at least one of red emitting or green emitting pixels in the display portion to emit light during the second period of time, to detect the blood in the finger and capture the second image of the blood in the finger.

19. The device of claim 1 wherein the detection circuitry is configured for generating a difference between the first image and the second image to obtain a resulting image at a desired depth into the finger.

20. The device of claim 1 wherein the detector subtracts the first signals generated by some photodetectors from the first signals generated by other ones of the photodetectors so that the differences correlate to absorption of the wavelengths of interest.

* * * * *